US008987263B2

(12) United States Patent
Shinitzky et al.

(10) Patent No.: US 8,987,263 B2
(45) Date of Patent: Mar. 24, 2015

(54) BASIC ESTERS OF FATTY ALCOHOLS AND THEIR USE AS ANTI-INFLAMMATORY OR IMMUNOMODULATORY AGENTS

(76) Inventors: Meir Shinitzky, Kfar Shmaryahu (IL); Irun R. Cohen, Rehovot (IL); Raanan Margalit, Ganei Yochanan (IL); Yaacov Herzig, Raanana (IL); Jeffrey Sterling, Jerusalem (IL); Gyorgy Toth, Nyiregyhaza (HU); Istvan Miskolczi, Debrecen (HU); Ferenc Rantal, Debrecen (HU); Tivadar Tamas, Debrecen (HU)

( * ) Notice: Subject to any disclaimer, the term of this patent is extended or adjusted under 35 U.S.C. 154(b) by 1544 days.

(21) Appl. No.: 10/530,776

(22) PCT Filed: Oct. 9, 2003

(86) PCT No.: PCT/IL03/00820

§ 371 (c)(1),
(2), (4) Date: Dec. 19, 2005

(87) PCT Pub. No.: WO2004/032824

PCT Pub. Date: Apr. 22, 2004

(65) Prior Publication Data

US 2006/0173053 A1    Aug. 3, 2006

Related U.S. Application Data

(60) Provisional application No. 60/417,157, filed on Oct. 10, 2002.

(51) Int. Cl.
| | | |
|---|---|---|
| *A61K 31/5377* | (2006.01) |
| *A61K 31/495* | (2006.01) |
| *A61K 31/131* | (2006.01) |
| *C07D 295/00* | (2006.01) |
| *C07C 211/01* | (2006.01) |
| *A61K 31/195* | (2006.01) |
| *A61K 31/22* | (2006.01) |
| *A61K 31/221* | (2006.01) |
| *A61K 31/222* | (2006.01) |
| *A61K 31/223* | (2006.01) |
| *A61K 31/44* | (2006.01) |
| *A61K 31/4425* | (2006.01) |
| *A61K 45/06* | (2006.01) |

(52) U.S. Cl.
CPC .............. *A61K 31/195* (2013.01); *A61K 31/22* (2013.01); *A61K 31/221* (2013.01); *A61K 31/222* (2013.01); *A61K 31/223* (2013.01); *A61K 31/44* (2013.01); *A61K 31/4425* (2013.01); *A61K 45/06* (2013.01)
USPC ........ 514/238.8; 544/171; 544/399; 564/463; 514/252.12; 514/739

(58) Field of Classification Search
USPC .......... 514/238.8, 252.12, 739; 544/171, 399; 564/463
See application file for complete search history.

(56) References Cited

U.S. PATENT DOCUMENTS

| | | | |
|---|---|---|---|
| 3,592,930 A | 7/1971 | Katz et al. | |
| 3,629,111 A * | 12/1971 | Cramer ........................... | 252/75 |
| 4,152,423 A | 5/1979 | Adam et al. | |
| 4,258,029 A | 3/1981 | Moloney et al. | |
| 4,428,932 A * | 1/1984 | Overell ....................... | 424/275.1 |
| 4,826,818 A * | 5/1989 | Mori et al. ....................... | 514/21 |
| 5,194,451 A | 3/1993 | Katz et al. | |
| 5,340,588 A | 8/1994 | Domb | |
| 5,540,931 A | 7/1996 | Hewitt et al. | |
| 5,807,820 A | 9/1998 | Elias | |
| 5,817,629 A | 10/1998 | Warren et al. | |
| 5,910,306 A | 6/1999 | Alving et al. | |
| 5,968,524 A | 10/1999 | Watson et al. | |
| 5,984,764 A | 11/1999 | Saito et al. | |
| 6,114,337 A | 9/2000 | Pugliese | |
| 6,118,020 A | 9/2000 | Buyuktimkin et al. | |
| 6,204,420 B1 * | 3/2001 | Miller et al. ....................... | 585/4 |
| 6,210,700 B1 | 4/2001 | Valente et al. | |
| 6,280,755 B1 | 8/2001 | Berger et al. | |
| 6,331,568 B1 | 12/2001 | Horrobin | |
| 6,365,628 B1 | 4/2002 | Berge | |
| 6,458,772 B1 | 10/2002 | Zhou et al. | |
| 6,673,908 B1 | 1/2004 | Stanton, Jr. | |

(Continued)

FOREIGN PATENT DOCUMENTS

| | | | | |
|---|---|---|---|---|
| EP | 0 955 046 | | 11/1999 | |
| FR | 2383662 A1 * | | 3/1977 | .................... 554/100 |
| GB | 1 436 614 | | 5/1976 | |

(Continued)

OTHER PUBLICATIONS

STN, CAplus registry No.: RN 1195333-35-7, Accessed Mar. 6, 2012.*
Nicolaou, Anna. Lipidic mimetics as inhibitors of pancreatic phospholipase A2. Biochemical Society Transactions. 23 (1995) 614S.*
Ito et al. [Ito, Nobuyuki. Cancer Science 94(1), (2003) 3-8.*
Database Registry Chemical Abstracts Service, Columbus, Ohio, Accession No. RN 10025-06-6, Entered STN: Nov. 16, 1984.*
International Search Report issued by the International Searching Authority issued Jul. 15, 2004, in connection with related International Application No. PCT/IL2003/000820.

(Continued)

*Primary Examiner* — Samantha Shterengarts
(74) *Attorney, Agent, or Firm* — John P. White; Cooper & Dunham LLP

(57) ABSTRACT

Basic esters of fatty alcohols of the general formula: R1-O—CO-A or pharmaceutically acceptable salts thereof, wherein R1 is $C_{12}$-$C_{24}$ alkyl or $C_{10}$-$C_{24}$ alkenyl, and A is a residue containing at least one acyclic or cyclic amino group and/or at least one heteroaromatic ring containing a tertiary or quaternary nitrogen atom, are anti-inflammatory and immunomodulatory agents, useful in the treatment of immunologically-mediated inflammation, as adjuvants for antigens involved in both cellular and humoral responses.

17 Claims, 10 Drawing Sheets

(56) References Cited

U.S. PATENT DOCUMENTS

| | | |
|---|---|---|
| 2004/0247604 A1 | 12/2004 | Cohen et al. |
| 2006/0183797 A1 | 8/2006 | Cohen et al. |

FOREIGN PATENT DOCUMENTS

| | | |
|---|---|---|
| JP | 555-0-0167 | 10/1979 |
| JP | 61-103826 | 5/1986 |
| JP | 671-1-3826 | 5/1986 |
| JP | 10101630 | 4/1998 |
| JP | 113-4-3235 | 12/1999 |
| JP | P2001-503743 A | 3/2001 |
| JP | 2002097137 | 4/2002 |
| WO | WO 91/16926 | 11/1991 |
| WO | WO 93/20100 | 10/1993 |
| WO | WO 98/11887 | 3/1998 |
| WO | WO 98/16216 | 4/1998 |
| WO | WO 98/52556 | 11/1998 |
| WO | WO9904632 | 2/1999 |
| WO | WO0100139 | 1/2001 |
| WO | WO02083058 | 10/2002 |
| WO | WO02083122 | 10/2002 |
| WO | WO 2004/000271 | 12/2003 |
| WO | WO 02/32824 | 4/2004 |
| WO | WO/2008/106091 | 9/2008 |
| WO | WO/2008/106092 | 9/2008 |

OTHER PUBLICATIONS

U.S. Appl. No. 12/072,304, filed Feb. 25, 2008, Hayardeny-Nisimov.
U.S. Appl. No. 12/072,405, filed Feb. 25, 2008, Herzig et al.
International Search Report issued on Jun. 2, 2008 in connection with PCT/US08/02471, international filing date Feb. 25, 2008.
International Search Report issued on Jun. 18, 2008 in connection with PCT/US08/02472, international filing date Feb. 25, 2008.
U.S. Appl. No. 10/474,447, filed May 10, 2004, Cohen et al.
European Search Report (EP 02/761953), issued Jul. 1, 2004.
Supplemental European Search Report issued on Nov. 11, 2004 in connection with European Patent Application No. 002 72 4588.5;.
International Search Report issued on Sep. 11, 2002 in connection with PCT Application No. PCT/IL02/00294, International filing date Oct. 24, 2004.
International Preliminary Examination Report issued Jun. 24, 2003 in connection with PCT Application No. PCT/IL02/00294.
International Search Report issued on Feb. 20, 2003 in connection with PCT Application No. PCT/IL02/00295, International filing date Apr. 11, 2002.
International Preliminary Examination Report issued Feb. 19, 2004 in connection with PCT Application No. PCT/IL02/00295, International filing date Apr. 11, 2002.
Sands J. (1978) "Extreme Sensitivity of Enveloped Viruses, Including Herpes Simplex, to Long-Chain Unsaturated Monoglycerides and Alcohols" *Antimicrobial Agents and Chemotherapy* 15(1):67-63; and.
Snipes, W. (1977) "Inactivation of Lipid-Containing Viruses by Long-Chain Alcohols" *Antimicrobial agents and Chemotherapy* 11(1):98-104.
Office Action issued on Jun. 29, 2006 by the U.S. Patent and Trademark Office in connection with U.S. Appl. No. 10/474,448.
Office Action issued on Nov. 2, 2006 by the U.S. Patent and Trademark Office in connection with U.S. Appl. No. 10/474,448.
Office Action issued on Dec. 13, 2007 by the U.S. Patent and Trademark Office in connection with U.S. Appl. No. 10/474,448.
Office Action issued on Jul. 17, 2006 by the U.S. Patent and Trademark Office in connection with U.S. Appl. No. 10/474,447.
Office Action issued on Dec. 28, 2006 by the U.S. Patent and Trademark Office in connection with U.S. Appl. No. 10/474,447.
Final Office Action issued on Nov. 16, 2007 by the U.S. Patent and Trademark Office in connection with U.S. Appl. No. 10/474,447.
Office Action issued on Nov. 6, 2008 by the U.S. Patent and Trademark Office in connection with U.S. Appl. No. 10/474,447.
Final Office Action issued on May 11, 2009 by the U.S. Patent and Trademark Office in connection with U.S. Appl. No. 10/474,447.

MedlinePlus® "Medical Encyclopedia: Autoimmune disorders", 2007, downloaded from "htt;://www.nlm.nih.gov/medlineplus/ency/article/000816.htm" on Apr. 30, 2009, pp. 1-3 of 3.
Oct. 27, 2010 response to Jun. 28, 2010 Office Action filed in connection with U.S. Appl. No. 12/072,405.
Oct. 25, 2010 Examiner Interview in connection with U.S. Appl. No. 12/072,405.
Parant M A et al. (1980) "Immunostimulant activities of a lipophilic muramyl dipeptide derivative and of desmuramyl peptidolipid analogs". Infection and Immunity 27(3): 826-31.
PCT International Preliminary Report on Patentability issued on Aug. 26, 2009 in connection with PCT App No. PCT/US2008/002472, international filing date Feb. 25, 2008.
PCT International Preliminary Report on Patentability issued on Aug. 26, 2009 in connection with PCT App No. PCT/US2008/002471, international fililng date Feb. 25, 2008.
Written Opinion of the International Searching Authority issued Jun. 18, 2008 in connection with PCT App No. PCT/US2008/002472, international filing date Feb. 25, 2008.
Written Opinion of the International Searching Authority issued Jun. 2, 2008 in connection with PCT App No. PCT/US2008/002471, international filing date Feb. 25, 2008.
Aug. 19, 2009 Office Action issued by the U.S. Patent and Trademark Office in connection with U.S. Appl. No. 12/072,304.
Feb. 26, 2010 Office Action issued by the U.S. Patent and Trademark Office in connection with U.S. Appl. No. 12/072,304.
Apr. 16, 2008 Office Action issued by the U.S. Patent and Trademark Office in connection with U.S. Appl. No. 10/474,447.
Nov. 16, 2009 Advisory Action issued by the U.S. Patent and Trademark Office in connection with U.S. Appl. No. 10/474,447.
Dec. 16, 2009 Office Action issued by the U.S. Patent and Trademark Office in connection with U.S. Appl. No. 10/474,447.
Oct. 23, 2009 Office Action issued by the U.S. Patent and Trademark Office in connection with U.S. Appl. No. 12/072,405.
Feb. 1, 2010 Office Action issued by the U.S. Patent and Trademark Office in connection with U.S. Appl. No. 12/072,405.
Jun. 28, 2010 Final Office Action issued by the U.S. Patent and Trademark Office in connection with U.S. Appl. No. 12/072,405.
Aug. 30, 2006 Response to Jun. 29, 2006 Office Action filed in connection with U.S. Appl. No. 10/474,448.
Mar. 30, 2007 Amendment in Response to Nov. 2, 2006 Office Action filed in connection with U.S. Appl. No. 10/474,448.
Sep. 11, 2009 Amendment in Response to Aug. 19, 2009 Office Action filed in connection with U.S. Appl. No. 12/072,304.
Jun. 23, 2010 Response to Feb. 26, 2010 Office Action filed in connection with U.S. Appl. No. 12/072,304.
Aug. 17, 2006 Response to Jul. 17, 2006 Office Action filed in connection with U.S. Appl. No. 10/474,447.
Mar. 28, 2007 Amendment in Response to Dec. 28, 2006 Office Action filed in connection with U.S. Appl. No. 10/474,447.
Feb. 15, 2008 Amendment Under C.F.R. § 1.116 in Response to Nov. 16, 2007 Final Office Action filed in connection with U.S. Appl. No. 10/474,447.
Jun. 16, 2008 Response to Apr. 16, 2008 Restriction Requirement filed in connection with U.S. Appl. No. 10/474,447.
Feb. 6, 2009 Amendment in Response to Nov. 6, 2008 Office Action filed in connection with U.S. Appl. No. 10/474,447.
Aug. 11, 2009 Amendment Under C.F.R. § 1.116 in Response to May 11, 2009 Final Office Action filed in connection with U.S. Appl. No. 10/474,447.
Mar. 15, 2010 Amendment in Response to Dec. 16, 2009 Office Action filed in connection with U.S. Appl. No. 10/474,447.
Nov. 20, 2009 Response to Oct. 23, 2009 Office Action filed in connection with U.S. Appl. No. 12/072,405.
Apr. 30, 2010 Response to Feb. 1, 2010 Office Action filed in connection with U.S. Appl. No. 12/072,405.
Grouiller A, et al. (2002) "Analogues et derives de la p.chlorophenylalenine: Synthese, propietes. . . (Abstract in English)". Eur. J. Med. Chem—Chimica Therapeutica 139-146.
Johnson, David W. (2001) "Analysis of alchohols as dimethylglycine esters, by electrospray ionization tandem mass spectrometry". Journal of Mass Spectrometry 36:277-283.

(56) References Cited

OTHER PUBLICATIONS

Limanov V.E et al. (1984) "Synthesis and Bactericidal Activity of Higher Amino-Acid Ester . . ." Khimiko-Framatsevticheskii Zhurnal, vol. 18, NR. 10, pp. 1214-1217.
MedlinePlus® Health, "Multiple . . .", updated Mar. 23, 2001, from "Http://web.archive.org/web/20010617130710/http://www.nlm.nih.gov/medlineplus/ency/article/000737.htm" pp. 1-4 of 4.
Michiko Watanabe et al. (1988) "Alkylbenzyldimethylammonium Salts as Inhibitors for the Ice Nucleating Activity of Erwinia ananas". Agric. Biol. Chem., 52(1):201-206.
Ohtani, Noritaka et al. (1995) "Reactions of Amino Acid Decyl Esters with Nucleophiles Catalyzed by Polymer-Supported . . .". Bull. Chem. Soc. Jpn., 68:1669-1675.
Penney Christoper L., et al. (1994) "Further studies on the adjuvanticity of stearyl tyrosine and amide analogues". Vaccine, 12(7):629-632.
Schulz E., et al. (1982) "Pharmacological Properties of D, L-2-Phenylglycine Alkylesuers with Special . . ." Department of Pharmicology and Toxiocology, 119-128.
Schulz, Elisabeth et al. (1983) "Synthese and einige pharmakologische Eigenschaften von Alkylestern verschiedener DL—Phenylaminosauren". Pharmazie, 38:310-313.
Takakura, Isamu et al. (1990) "Pharmaceuticals containing piroxicam plasters and fatty acids (Abstract in English)".
WebMD®, "Osteoarthritis Guide", 2007, downloaded from "http://www.webmd.com/osteoarthritis/guide/arthritis-basics" on Dec. 8, 2009, pp. 1-4 of 4.
Apr. 5, 2011 Office Action issued by the U.S. Patent and Trademark Office in connection with 10/474,447.
Grouiller A, et al. (1980) "Analogues et derives de la p. chlorophenyialenine: Synthese, propietes . . .(Abstract in English)". Eur. J. Med. Chem—Chimica Therapeutica 139-146.

* cited by examiner

BASIC ESTERS OF FATTY ALCOHOLS AND THEIR USE AS ANTI-INFLAMMATORY OR IMMUNOMODULATORY AGENTS

This application is a §371 National Stage of PCT International Application No. PCT/IL2003/000820, filed Oct. 9, 2003, claiming priority of U.S. Provisional Application No. 60/417,157, filed Oct. 10, 2002, the contents of which are hereby incorporated by reference.

FIELD OF THE INVENTION

The present invention relates to basic esters of fatty alcohols and their use as anti-inflammatory and immunomodulatory agents, particularly useful in the treatment of immunologically-mediated inflammation, and as adjuvants for antigens involved in both cellular and humoral responses.

Abbreviations: AA: adjuvant arthritis: CFA: complete Freund's adjuvant; DTH: delayed-type hypersensitivity EAE: experimental autoimmune encephalomyelitis; GA: glatiramer acetate; IFA: incomplete Freund's adjuvant; IV: intravenously; MBP: myelin basic protein; MS: multiple sclerosis; MSCH: mouse spinal cord homogenate; OA: oleyl alcohol; PBS: phosphate-buffered saline; SC: subcutaneously.

BACKGROUND OF THE INVENTION

1. Inflammation

Inflammation is commonly divided into three phases: acute inflammation, the immune response and chronic inflammation. Acute inflammation is the initial response to tissue injury and is mediated by the release of histamine, serotonin, bradykinin, prostaglandins and leukotrienes. The immune response, usually preceded by the acute inflammation phase, occurs when immunologically competent cells are activated in response to foreign organisms or antigenic substances liberated during the acute or chronic inflammatory response. The outcome of the immune response for the host may be beneficial, as it causes invading organisms to be phagocytosed or neutralized. However, the outcome may be deleterious if it leads to chronic inflammation without resolution of the underlying injurious process as occurs in rheumatoid arthritis.

The treatment of patients with inflammation leads to the slowing or arrest of the tissue-damaging process as well as the relief of pain, which is the presenting symptom and the major continuing complaint of the patient.

Anti-inflammatory agents are usually classified as steroidal or glucocorticoids and nonsteroidal anti-inflammatory agents (NSAIDs). The glucocorticoids are powerful anti-inflammatory agents but the high toxicity associated with chronic corticosteroid therapy inhibits their use except in certain acute inflammatory conditions. Therefore, the nonsteroidal anti-inflammatory drugs have assumed a major role in the treatment of chronic conditions such as rheumatoid arthritis.

Among the non-steroidal anti-inflammatory agents are included derivatives of aminoarylcarboxylic acids, arylacetic acids, arylbutyric acids, arylcarboxylic acids, arylpropionic acids, pyrazole, pyrazolone, salicylic acid and some other derivatives of different chemical structure, including specific anti-arthritic/anti-rheumatic agents.

It would be highly desirable to provide new nonsteroidal anti-inflammatory agents that could serve as alternatives to current anti-inflammatory drugs.

2. Vaccines and Adjuvants

Lymphocytes are the central cells of the immune system, responsible for acquired immunity and the immunologic attributes of diversity, specificity, memory, and self/non-self recognition. Mature B cells are distinguished from other lymphocytes by their synthesis and display of membrane-bound immunoglobulin (antibody) molecules, which serve as receptors for antigens. Interaction between antigen and the membrane-bound antibody on a mature naive B cell, results in the activation and differentiation of B-cell clones of corresponding specificity and the consequent production of B cell clones lacking the membrane-bound antibody, but which secrete antibody molecules with the same antigen-binding specificity.

T lymphocytes, like B lymphocytes, have membrane receptors for antigens. However, unlike the membrane-bound antibody on B cells, the T-cell receptor (TCR) does not recognize free antigen. Instead, the TCR recognizes only antigen that is bound to a self-molecule encoded by genes within the major histocompatibility complex (MHC). To be recognized by most T cells, the antigen must be displayed together with MHC molecules on the surface of antigen-presenting cells (APC) or on virus-infected cells, cancer cells, and grafts.

Like B cells, T cells express distinctive membrane molecules. All T-cell subpopulations express the TCR, a complex of polypeptides that includes CD3, and most can be distinguished by the presence of one or the other of two membrane molecules, CD4 and CD8. T cells that express the membrane glycoprotein molecule CD4 are restricted to recognizing antigen bound to class II MHC molecules, whereas T cells expressing CD8, a dimeric membrane glycoprotein, are restricted to recognition of antigen bound to class I MHC molecules.

In general, expression of CD4 and of CD8 also defines two major subpopulations of T lymphocytes. $CD4^+$ T cells generally function as T helper ($T_H$) cells and are class-II restricted; $CD8^+$ T cells generally function as T cytotoxic ($T_C$) cells and are class-I restricted.

$T_H$ cells are activated by recognition of an antigen-class II MHC complex on an antigen-presenting cell. After activation, the $T_H$ cell begins to divide and gives rise to a clone of effector cells, each specific for the same antigen-class II MHC complex. These $T_H$ cells secrete various cytokines, which play a central role in the activation of B cells, T cells, and other cells that participate in the immune response.

Changes in the pattern of cytokines produced by $T_H$ cells can change the type of immune response that develops among other leukocytes. Thus $T_H$ cells have been divided into two groups by the characteristic cytokines they secrete when activated: the $T_H1$ response produces a cytokine profile that supports inflammation and activates mainly certain T cells and macrophages whereas the $T_H2$ response activates mainly B cells and immune responses that depend upon antibodies. Thus, $T_H1$ cells secrete IL-2, which induces T-cell proliferation, and cytokines such as IFN-γ, which mediates tissue inflammation. $T_H2$ cells, in contrast, secrete IL-4, which activates B cells to secrete antibodies of certain IgG isotypes and suppresses the production of $T_H1$ inflammatory cytokines, and IL-10, which suppresses inflammatory cytokine production by macrophages, and thus indirectly reduces cytokine production by $T_H1$ cells, and affects antigen-presenting cells by down-regulating class II MHC expression.

Autoimmunity results from an inappropriate response of the immune system against self-components leading to activation of self-reactive clones of T or B cells, and generation of humoral or cell-mediated responses against endogenous antigens, with consequent injury to cells, tissues and organs.

Sometimes, the damage is caused by antibodies as in the autoimmune disorders Addison's disease, autoimmune anemia, e.g. autoimmune hemolytic anemia and pernicious anemia, Hashimoto's thyroiditis and scleroderma.

Many autoimmune disorders e.g. insulin-dependent diabetes mellitus (IDDM or type I diabetes), multiple sclerosis, rheumatoid arthritis and autoimmune thyroiditis are characterized by tissue destruction mediated by T cells activated by an endogenous antigen. These immune responses to self-antigens are maintained by the persistent activation of the self-reactive T lymphocytes.

Autoimmune diseases can be divided into organ-specific autoimmune diseases, in which the immune response is directed to a target antigen unique to a single organ or gland, so that the manifestations are largely limited to that organ, and systemic autoimmune diseases, in which the response is directed toward a broad range of target antigens and involves a number of organs and tissues. Examples of organ-specific autoimmune diseases include insulin-dependent diabetes mellitus, multiple sclerosis, rheumatoid arthritis, thyroiditis, and myasthenia gravis, and examples of systemic autoimmune diseases include systemic lupus erythematosus and scleroderma.

It is the $T_H1$ cells which contribute to the pathogenesis of organ-specific autoimmune diseases. For example, there is strong evidence that, in mice, experimental autoimmune encephalomyelitis (EAE) is caused by $CD4^+$ $T_H1$ cells specific for the immunizing antigen, e.g. myelin basic protein (MBP) or proteolipid protein (PLP). The disease can be transferred from one animal into another by T cells from animals immunized with either MBP or PLP or by cloned T-cell lines from such animals. $T_H1$-type responses also appear to be involved in other T-cell mediated diseases or conditions such as contact dermatitis.

Most cases of organ-specific autoimmune diseases develop as a consequence of self-reactive $CD4^+$ T cells. Analysis of these T cells revealed that the $T_H1/T_H2$ balance can affect whether autoimmunity develops. $T_H1$ cells have been involved in the development of autoimmunity, whereas, in several cases, $T_H2$ cells not only protected against the induction of the disease but also against progression of established disease and in the induction and maintenance of allograft tolerance.

Several therapeutic approaches have been explored for treatment of autoimmune diseases. Identification and sequencing of various autoantigens have led to the development of new approaches to modulate autoimmune T-cell activity. Whole antigens involved in the pathogenesis of the autoimmune disease or peptides derived from their sequences have been proposed for the treatment of autoimmune diseases.

Synthetic peptides suitable for immunologically specific therapy of an autoimmune disease are peptides that are recognized by T cells involved in the pathogenesis of the autoimmune disease. These peptides may have a sequence consisting of a pathogenic sequence within the sequence of an antigen involved in the disease or may be an analogue thereof, in which sequence one or more native amino acid residues are substituted by different amino acid residues, particularly a so-called "altered peptide", which contains a single amino acid substitution in the epitope of the pathogenic native counterpart (i.e., the region that contacts the TCR), but have no alterations in the agretope (i.e., the region that contacts the MHC).

Each autoimmune disease will have its ideal peptide for use in therapy that is derived directly from the sequence of an antigen associated with the disease, or is an altered peptide, or another analogue thereof. Thus, a disease like multiple sclerosis (MS) involving T cells reactive to self-antigens such as myelin basic protein (MBP), myelin oligodendrocyte glycoprotein (MOG) and proteolipid protein (PLP), will require for its therapy a peptide of MBP, MOG or PLP or an analogue thereof; myasthenia gravis can be treated with a peptide from the acetylcholine receptor; thyroiditis with a peptide from thyroglobulin; diabetes type 1 with a peptide of glutamic acid decarboxylase (GAD) or a peptide from the insulin sequence; systemic lupus erythematosus with a peptide derived from the protein P53; and Guillain-Barré syndrome with a peptide from the myelin antigen P2.

In recent years, peptides derived from a pathogenic self-antigen associated with an autoimmune disease or analogues thereof have been proposed for treatment of the disease. For example, peptides derived from the human MBP sequence (U.S. Pat. No. 5,817,629; U.S. Pat. No. 6,252,040) and analogues thereof (U.S. Pat. No. 5,948,764; U.S. Pat. No. 6,329,499) have been described for treatment of multiple sclerosis; peptide analogues of the 65 kD isoform of human GAD and of insulin have been proposed for treatment of diabetes (U.S. Pat. No. 5,945,401 and U.S. Pat. No. 6,197,926, respectively); and an autoantigen or a fragment thereof have been described for the treatment of uveoretinitis (U.S. Pat. No. 5,961,977). Each and all of the patents cited above are hereby incorporated by reference herein as if fully disclosed herein.

For each of the various autoimmune diseases, it would be desirable to administer the relevant peptide in an adjuvant that would activate T cells of the anti-inflammatory $T_H2$ phenotype. This would be expected to arrest the autoimmune process. There are also situations not involving therapy of an autoimmune disease in which it would be useful to activate specific T cells with a $T_H2$ phenotype. However, treatment involving self-antigens must be done in adjuvants that do not induce $T_H1$-type immunity that might activate dangerous $T_H1$ autoimmunity in the treated subject. Thus, there is a need to identify adjuvants capable of being combined with specific antigens that will induce non-inflammatory $T_H2$-type T cells.

Adjuvants, by their nature, are non-specific immunomodulators. An adjuvant suitable for the purposes outlined above would be a non-specific immunomodulator that could be combined in a therapeutic vaccination with an antigen or other molecule so as to induce the activation of specific T cells of the desired anti-inflammatory phenotype.

Several peptides suitable for the therapy of T-cell mediated diseases, disorders or conditions such as autoimmune diseases were shown to be effective when administered to mice subcutaneously (SC) in an oil vehicle such as an emulsion of mineral oil known as incomplete Freund's adjuvant (IFA). However, IFA as well as complete Freund's adjuvant (CFA; a preparation of mineral oil containing various amounts of killed organisms of Mycobacterium) are not allowed for human use because the mineral oil cannot be degraded in the body.

It would be highly desirable to discover effective vehicles for peptide therapy that would be degradable and act as an adjuvant that serves as a carrier, or depot or immune potentiator/enhancer.

3. References Related to the Art

Some fatty alcohols and esters of fatty acids have been described as solvents or emulsifiers for use in pharmaceutical compositions. For example, cetyl alcohol may be used in pharmaceutical compositions as emulsifying and stiffening agent (The Merck Index, 2001, 13$^{th}$ edition, pp. 347-8, #2037), oleyl alcohol may be used as a carrier for medicaments (The Merck Index, 2001, 13$^{th}$ edition, p. 1222, #6900), and alkyl esters of oleic acid may be used as solvents for medicaments (The Merck Index, 2001, 13th edition, p. 6899, #6898).

A mixture of higher aliphatic primary alcohols, primarily isolated from beeswax, was described as having moderate anti-inflammatory activity. The composition of such a mixture was not disclosed (Rodriguez et al., 1998).

The mass spectra of nicotinates of long chain alcohols, e.g. octadecyl and (Z)-9-octadecen-1-yl nicotinates, have been studied to elucidate the structure of long chain alcohols (Vetter and Meister, 1981). No biologic activity was assigned to the compounds.

Esters of 4-aminomethyl-benzoic acid (PAMBA) with $C_6$-$C_{16}$ saturated alcohols, e.g. decyl, undecyl, tetradecyl and hexadecyl alcohols, have been tested for their antifibrinolytic activity and found to be not active (Markwardt et al., 1966). PAMBA esters with short chain alcohols were found to be able to decrease the proliferation of in vitro cultivated endothelial cells, the hexyl ester being the more effective (Beyer and Pilgrim, 1991).

Alkyl N,N-disubstituted amino acids, e.g. alkyl N,N-dimethylamino acetate wherein the alkyl is octyl, decyl, dodecyl, or tetradecyl, and decyl(4-methyl-1-piperazinyl)acetate, have been described as transdermal penetration enhancers for indomethacin and possibly for other drugs (Wong et al., 1989; U.S. Pat. No. 4,980,378).

Complexes for use in gene therapy comprising a therapeutically active substance and a cationic lipid such as quaternary piperazinium compounds substituted at both the 1 and 4 positions by a methyl and an oleyloxycarbonylmethyl radicals are described in U.S. Pat. No. 6,291,423.

Esters of N,N-dimethyl-aminoacetic acid with long chain alkanols, e.g. tetradecyl, cetyl and stearyl alcohols, and alkenols, are described in JP 2000-302650 for use in hair cosmetics. The oleyl ester is not specifically disclosed.

Betaine [(carboxymethyl)trimethylammonium hydroxide inner salt] esters with long-chain alcohols such as decyl, lauryl, myristyl, pamityl, stearyl and oleyl alcohol were prepared and their pharmacodynamic properties have been studied (Metayer and Jacob, 1952), or their activity as biocides for cooling water treatment was tested (Rucka et al., 1983).

Quaternary ammonium salts of lauryl, myristyl and cetyl esters of N-carboxymethyl-piperidine, -piperazine and -morpholine compounds were described as germicides (Smith et al., 1951).

Stearyl esters of amino acids, e.g. glycine, phenylglycine, alanine, valine, leucine, lysine, proline, phenylalanine, and tyrosine, and stearyl esters of peptides have been proposed as adjuvants for bacterial and viral human vaccines (Penney et al., 1985, 1993; Nixon-George et al., 1990).

Esters of DL-ω-phenyl-amino acids with $C_4$-$C_{10}$ alkanols, such as DL-2-phenylglycine octyl or decyl ester or DL-2-(4-dimethylaminophenyl)glycine octyl ester have been described as antiphlogistic, antihistaminic, spasmolytic, antioxidant and anti-inflammatory (Schulz et al., 1982; Schewe et al., 1991; Kontogiorgis et al., 2001).

Higher alkyl esters of amino acid, e.g. lauryl, myristyl, cetyl and stearyl esters of glycine, phenylglycine, alanine, valine, norvaline, leucine, isoleucine, lysine, and phenylalanine, and their N-lower alkyl derivatives are described in U.S. Pat. No. 3,821,403 (Misato et al., 1974) as useful for control of plant diseases.

SUMMARY OF THE INVENTION

It has now been found, in accordance with the present invention, that certain esters of long-chain fatty alcohols with carboxylic acids containing at least one basic group, act as anti-inflammatory immunomodulators and, therefore, can be used for the treatment of inflammation, particularly immunologically-mediated inflammation, as well as adjuvants in combination with specific antigens involved in both cellular and humoral responses, wherein said adjuvant serves as a carrier, or as depot or as immune potentiator/enhancer.

In one aspect, the present invention relates to the use of a compound of the general formula I:

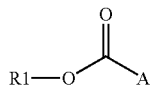

or of a pharmaceutically acceptable salt thereof, wherein R1 is $C_{12}$-$C_{24}$ alkyl or $C_{10}$-$C_{24}$ alkenyl, and A is a residue containing at least one acyclic or cyclic amino group and/or at least one heteroaromatic ring containing a tertiary or quaternary nitrogen atom, for the preparation of a pharmaceutical composition for treatment of inflammation.

In another aspect, the present invention relates to the use of an adjuvant of the general formula Ia:

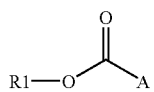

or of a pharmaceutically acceptable salt thereof, wherein R1 is $C_{10}$-$C_{24}$ alkyl or $C_{10}$-$C_{24}$ alkenyl, and A is a residue containing at least one acyclic or cyclic amino group and/or at least one heteroaromatic ring containing a tertiary or quaternary nitrogen atom, but excluding the compounds wherein R1 is $C_{18}$ alkyl and A is a residue containing at least one acyclic amino group or —CO-A is the residue of proline, for the preparation of a therapeutic preparation further comprising an antigen.

The antigen to be used with the adjuvant of the general formula Ia may be an antigen involved in autoimmune diseases, in different types of cancer such as melanoma, and in infectious diseases such as bacterial and viral infections. The therapeutic preparation comprising such an antigen and the adjuvant of the invention may be particularly useful to activate T cells for the purpose of therapy of autoimmune diseases and for T-cell mediated immune effects that need preferably a $T_H2$-type immune response.

Some of the compounds of the formulas above, as defined hereinafter, are novel and as such constitute a further aspect of the present invention.

DETAILED DESCRIPTION OF THE INVENTION

Figure 1:
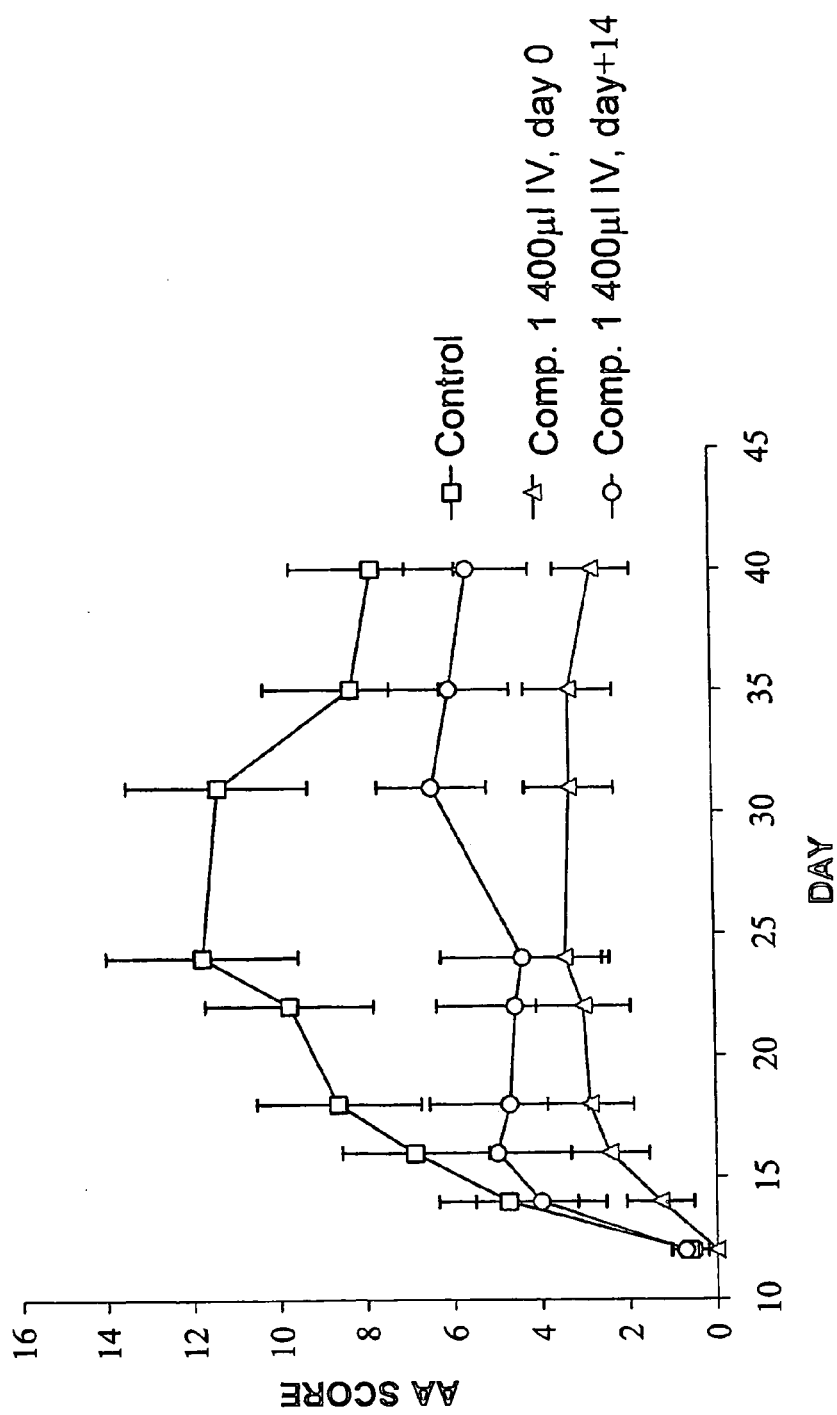
FIG. 1 shows the effect of N,N-dimethyl-aminoacetic acid octadec-(Z)-9-enyl ester (Compound 1) on adjuvant arthritis (AA). Compound 1 was administered intravenously (IV) to Lewis rats on the day of immunization (day 0, triangles) or on day 14, after the onset of AA (day +14, circles).

According to one aspect, the present invention provides the use of a compound of the general formula I:

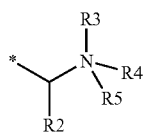

[I]

or of a pharmaceutically acceptable salt thereof, wherein R1 is $C_{12}$-$C_{24}$ alkyl or $C_{10}$-$C_{24}$ alkenyl, and A is a residue containing at least one acyclic or cyclic amino group and/or at least one heteroaromatic ring containing a tertiary or quaternary nitrogen atom, for the preparation of a pharmaceutical composition for treatment of inflammation.

In one embodiment of this aspect of the invention, in said anti-inflammatory compound of formula I, the residue A is selected from the group consisting of:

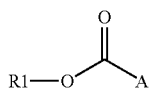

(i)

wherein R2 is H, $C_1$-$C_6$ alkyl, aryl, or aralkyl, wherein any aryl moiety may be unsubstituted or substituted by nitro, cyano, halo, hydroxy, NR6R7, or CR8R8NR6R7; R3 is H, a pair of electrons or $C_1$-$C_6$ alkyl; R4 and R5 each independently is H or $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl;

(ii) phenyl substituted by NR6R7 or CR8R8NR6R7, wherein R6, R7 and R8 each independently is H or $C_1$-$C_6$ alkyl; and

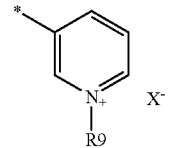

(iii)

wherein R9 is H, lower alkyl or indolyl($C_1$-$C_4$)alkyl, and X⁻ is a counter ion, or R9 is a pair of electrons and X is absent.

In another aspect, the present invention provides the use of an adjuvant of the general formula Ia:

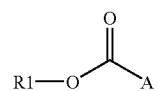

[Ia]

or of a pharmaceutically acceptable salt thereof, wherein R1 is $C_{10}$-$C_{24}$ alkyl or $C_{10}$-$C_{24}$ alkenyl, and A is a residue containing at least one acyclic or cyclic amino group and/or at least one heteroaromatic ring containing a tertiary or quaternary nitrogen atom, but excluding the compounds wherein R1 is $C_{18}$ alkyl and A is a residue containing at least one acyclic amino group or —CO-A is the residue of proline, for the preparation of a therapeutic preparation further comprising an antigen.

In one embodiment of this aspect of the invention, in said adjuvant of formula Ia, the residue A is selected from the group consisting of:

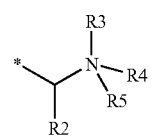

(i)

wherein R2 is H, $C_1$-$C_6$ alkyl, aryl, or aralkyl, wherein any aryl moiety may be unsubstituted or substituted by nitro, cyano, halo, hydroxy, NR6R7, or CR8R8NR6R7; R3 is H, a pair of electrons or $C_1$-$C_6$ alkyl; R4 and R5 each independently is H or $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl, provided that R4 and R5 are not H or $C_1$-$C_6$ alkyl when R1 is octadecyl; and R6, R7 and R8 each independently is H or $C_1$-$C_6$ alkyl;

(ii) phenyl substituted by NR6R7 or CR8R8NR6R7, wherein R6, R7 and R8 each independently is H or $C_1$-$C_6$ alkyl; and

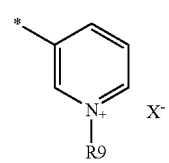

(iii)

wherein R9 is H, $C_1$-$C_6$ alkyl or indolyl($C_1$-$C_4$)alkyl, and X⁻ is a counter ion, or R9 is a pair of electrons and X is absent.

In a further aspect, the present invention relates to novel compounds of the general formula:

R1-O—CO-A wherein (i) R1 is $C_{20}$-$C_{24}$ alkyl or $C_{10}$-$C_{24}$ alkenyl, and A is a residue of the formula:

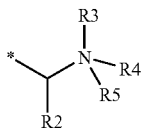

wherein R2 is H, $C_1$-$C_6$ alkyl, aryl, or aralkyl, wherein any aryl moiety may be unsubstituted or substituted by nitro, cyano, halo, hydroxy, NR6R7, or CR8R8NR6R7; R3 is H, a pair of electrons, or $C_1$-$C_6$ alkyl; R4 and R5 each independently is H or $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl; or (ii) R1 is $C_{18}$ alkyl and A is a residue of the formula:

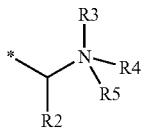

wherein R2 is H; R3 is a pair of electrons; and R4 and R5 together with the nitrogen atom to which they are attached form a 5-7 membered saturated ring optionally interrupted by an oxygen atom or by a nitrogen atom optionally substituted by $C_1$-$C_6$ alkyl; or (iii) R1 is $C_{12}$-$C_{16}$ alkyl and A is a residue of the formula:

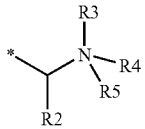

wherein R2 is unsubstituted aryl, or aryl or aralkyl wherein the aryl moiety is substituted by nitro, cyano, halo, hydroxy, NR6R7, or CR8R8NR6R7; R3 is H, a pair of electrons, or $C_1$-$C_6$ alkyl; R4 and R5 each independently is H or $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl; or (iv) R1 is $C_{10}$ alkyl and A is a residue of the formula:

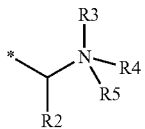

wherein R2 is $C_1$-$C_6$ alkyl; R3 is H, a pair of electrons, or $C_1$-$C_6$ alkyl; R4 and R5 each independently is H or $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl; or (v) R1 is $C_{10}$-$C_{24}$ alkyl or $C_{10}$-$C_{24}$ alkenyl and A is phenyl substituted by NR6R7 or CR8R8NR6R7, wherein R6, R7 and R8 each independently is H or $C_1$-$C_6$ alkyl, but excluding the compounds wherein R1 is $C_{10}$-$C_{16}$ alkyl and A is phenyl substituted by —$CH_2$—$NH_2$; or (vi) R1 is $C_{10}$-$C_{24}$ alkyl or $C_{10}$-$C_{24}$ alkenyl and A is a group of the formula:

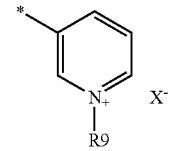

wherein R9 is $C_1$-$C_6$ alkyl or indolyl($C_1$-$C_6$)alkyl and $X^-$ is a counter ion; and pharmaceutically acceptable salts thereof.

For the sake of clarity, the mark * in all formulas herein in the specification and claims indicates the position linked to the —CO— of the R1-O—CO— group.

According to the invention, R1 is a $C_{10}$-$C_{24}$ alkyl or alkenyl for the adjuvants of formula Ia or R1 is a $C_{12}$-$C_{24}$ alkyl or $C_{10}$-$C_{24}$ alkenyl for the compounds of formula Ia for treatment of inflammation. In both cases, R1 is preferably $C_{12}$-$C_{20}$, more preferably $C_{16}$-$C_{18}$, most preferably $C_{18}$ alkyl or alkenyl. The alkyl groups may be straight or branched and are preferably selected from the group consisting of dodecyl, tetradecyl, hexadecyl and octadecyl such that the radicals R1-O— are derived from the saturated fatty alcohols lauryl alcohol, myristyl alcohol, cetyl alcohol (also known as palmityl alcohol), and stearyl alcohol, respectively. The alkenyl groups may have one or more double bonds and are preferably selected from the group consisting of hexadecenyl, octadecenyl, octadecadienyl and octadecatrienyl such that the radicals R1-O— are derived from the unsaturated fatty alcohols palmitoleyl alcohol or, preferably, from $C_{18}$-unsaturated fatty alcohols having one or more double bonds in the trans or, preferably, in the cis form, such as, but not being limited to, oleyl alcohol (cis-9-octadecenol), linoleyl alcohol (cis-9,12-octadecadienol), γ-linolenyl alcohol (cis-6,9,12-octadecatrienol) and linolenyl alcohol (cis-9,12,15-octadecatrienol). In a most preferred embodiment, R1 is the cis-9-octadecenyl radical also designated octadec-(Z)-9-enyl or oleyl.

The residue A may comprise a primary, secondary or tertiary amino group or a quaternary ammonium group that may be acyclic or cyclic. When the amino group is acyclic, the resulting compounds are esters of amino acids.

Thus, in one embodiment, in the compounds comprised in the pharmaceutical or therapeutic compositions of the invention or in some of the novel compounds of the invention, A is a radical of the formula:

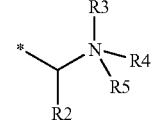

wherein R2 is H, $C_1$-$C_6$ alkyl, aryl, or aralkyl, wherein any aryl moiety may be unsubstituted or substituted by nitro, cyano, halo, hydroxy, NR6R7, or CR8NR6R7; R3 is H, a pair of electrons or $C_1$-$C_6$ alkyl; R4 and R5 each independently is $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl, with the limitations as defined hereinbefore and in the claims. For example, for the adjuvants of formula Ia and for the novel compounds, R4 and R5 cannot be H or $C_1$-$C_6$ alkyl when R1 is octadecyl (stearyl); for the novel compounds, wherein R1 is $C_{12}$-$C_{16}$ alkyl, R2 cannot be H, $C_1$-$C_6$ alkyl or unsubstituted aralkyl, or wherein R1 is $C_{10}$ alkyl, R2 cannot be H, aryl or aralkyl.

In one preferred embodiment, R2 is H. As used herein, $C_1$-$C_6$ alkyl refers to a straight or branched alkyl radical having 1 to 6 carbon atoms such as, but not limited to, methyl, ethyl, propyl, isopropyl, butyl, isobutyl, sec-butyl, pentyl and hexyl. The term "aryl" as used herein by itself or as part of the "aralkyl" radical refers to a $C_6$-$C_{10}$ aromatic carbocyclic radical such as phenyl and naphthyl. In a preferred embodiment, the aryl radical is phenyl. In the term "aralkyl", the alkyl refers as well to a $C_1$-$C_6$ alkyl radical. In a preferred embodiment, the aralkyl group is benzyl. In preferred embodiments, the phenyl and benzyl groups are unsubstituted or are substituted by hydroxy, for example, p-hydroxybenzyl.

Some compounds of the above formula wherein R3 is a pair of electrons and R4 and R5 are H, are esters of amino acids, for example, esters of glycine (R2 is H), alanine (R2 is methyl), valine (R2 is isopropyl), leucine (R2 is isobutyl), isoleucine (R2 is sec-butyl), phenylglycine (R2 is phenyl), phenylalanine (R2 is benzyl), tyrosine (R2 is p-hydroxybenzyl).

According to some embodiments of the invention, R4 and R5 together with the nitrogen atom to which they are attached may form a 5-7 membered saturated ring optionally interrupted by an oxygen atom or by a nitrogen atom such as pyrrolidine, azepine, and, preferably a 6-membered ring, more preferably piperidine, piperazine or morpholine. The piperazine ring may be substituted at the 4-position by a $C_1$-$C_6$ alkyl, preferably methyl.

In one preferred embodiment, R2 is H or phenyl, R3 is H, a pair of electrons or methyl, R4 and R5 are each H or methyl, or R4 and R5 together with the N atom to which they are attached form a morpholine or a piperazine ring optionally substituted at the nitrogen atom at position by methyl. Examples of compounds according to this embodiment for use as anti-inflammatory compounds and as adjuvants are the novel esters herein identified as Compounds 1, 3, 4, 7, 9, 11:
1. N,N-Dimethylamino-acetic acid octadec-(Z)-9-enyl ester
3. (4-Methyl-piperazin-1-yl)-acetic acid octadec-(Z)-9-enyl ester tartrate
4. (4-Methyl-piperazin-1-yl)-acetic acid octadecyl ester tartrate
7. 4-Methyl-4-octadec-(Z)-9-enyloxycarbonylmethyl-morpholin-4-ium chloride
9. Piperazin-1-yl-acetic acid octadec-(Z)-9-enyl ester bitartrate
11. α-Amino-α-phenyl-acetic acid octadec-(Z)-9-enyl ester HCl salt.

In another embodiment of the invention, A is phenyl substituted by NR6R7 or CR8R8NR6R7, wherein R6, R7 and R8 each independently is H or $C_1$-$C_6$ alkyl. In a preferred embodiment, A is phenyl substituted by CR8R8NR6R7, wherein R8 is H and R6 and R7 are each H or $C_1$-$C_6$ alkyl, preferably methyl. Examples of compounds according to this embodiment are the novel esters of 4-dimethylaminomethyl-benzoic acid herein identified as Compounds 5 and 10, for use both as anti-inflammatory agents and as adjuvants.

5. 4-dimethylaminomethyl-benzoic acid octadec-(Z)-9-enyl ester HCl
10. 4-dimethylaminomethyl-benzoic acid octadec-(E)-9-enyl ester HCl.

In yet a further embodiment of the invention, A is the pyridyl group:

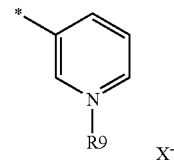

wherein R9 is a pair of electrons and X⁻ is absent, or R9 is methyl or indolylethyl and X⁻ is a counter ion selected from the group consisting of chloride, bromide, iodide and tosylate. These compounds are esters of nicotinic acid. Examples of compounds according to this embodiment are the compounds herein identified as Compounds 2, 6a, 6b, 6c, and 8, for use both as anti-inflammatory and as adjuvants, from which Compounds 6a, 6b, 6c, and 8 are novel compounds:
2. Nicotinic acid octadec-(Z)-9-enyl ester;
6a. 1-Methyl-3-octadec-(Z)-9-enyloxycarbonyl-pyridinium iodide;
6b. 1-Methyl-3-octadec-(Z)-9-enyloxycarbonyl-pyridinium chloride;
6c. 1-Methyl-3-octadec-(Z)-9-enyloxycarbonyl-pyridinium tosylate; and
8. 1-[(2-(1H-indol-3-yl)-ethyl]-3-octadec-(Z)-9-enyloxycarbonyl-pyridinium bromide;

The esters of the present invention are in general crystalline, non-hygroscopic and water-soluble and are more easily purified and formulated for oral and parenteral formulation than the starting saturated or cis-unsaturated alcohols.

Also contemplated by the present invention are pharmaceutically acceptable salts of the compounds of Formula I and Ia, both acid addition salts and quaternary salts of acyclic or cyclic ammonium groups or pyridinium salts with a counter ion. Pharmaceutically acceptable acid addition salts of the compounds include salts between the base and an inorganic acid such as hydrochloric, nitric, phosphoric, sulfuric, hydrobromic, hydriodic, phosphorous, and the like, as well as salts derived from an organic acid such as aliphatic mono- and dicarboxylic acids, phenyl-substituted alkanoic acids, hydroxyalkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, p-toluenesulfonate (tosylate), phenylacetate, citrate, lactate, maleate, tartrate, methanesulfonate, and the like.

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

In one embodiment of the invention, compounds of general formula I may be prepared by reacting the long-chain fatty alcohol such as oleyl alcohol with the suitable amino acid. Thus, oleyl alcohol is reacted with N,N-dimethylglycine to afford the compound herein designated Compound 1. In another embodiment, the long-chain fatty alcohol is reacted with an halide of nicotinic acid, for example, oleyl alcohol is reacted with nicotinoyl chloride to afford the compound herein designated Compound 2.

In a further embodiment, the long-chain fatty alcohol is reacted with halomethylacetic acid chloride and the resulting ester is then reacted with the suitable amine. For example, oleyl alcohol is reacted with chloroacetyl chloride and the resulting oleyl chloroacetic acid ester is reacted with piperazine or with N-methyl-morpholine, to give the free base that is then converted to the salt, e.g. Compound 3 or Compound 7, respectively. Similarly, stearyl alcohol is reacted with chloroacetyl chloride and the resulting stearyl chloroacetic acid ester is reacted with 4-methyl-piperazine to give the free base that is then converted to the salt, e.g. Compound 4.

Other methods according to the invention are described in the following examples and can be used to prepare similar compounds of Formula I herein. Reactions between oleyl alcohol and activated amino acids may be performed in a wide range of organic solvents, both polar, e.g. acetonitrile, chloroform, and non-polar, e.g. hexane, under a wide temperature range, from ambient to reflux, and over periods of time ranging from 1-2 hours to 1-2 days.

Quaternary pyridinium salts may be prepared either as described above, or by alkylating oleyl nicotinate using alkylating agents known to those skilled in the art such as alkyl halides, alkyl sulfonates and haloalkylindoles. Oleyl haloacetates may be reacted with amines in a wide range of organic solvents, both polar, e.g. acetonitrile, and non-polar, e.g. hexane, under a wide temperature range, from ambient to reflux, and over periods of time ranging from 1-2 hours to 1-2 days. The oily or low-melting free bases, obtained after suitable workup and purification are converted into pharmaceutically acceptable salts. The latter are usually high-melting and water soluble solids.

It should be noted that for the preparation of the esters of the invention wherein R1 is a cis-alkenyl group, the starting cis-unsaturated alcohol such as oleyl alcohol, may be used in a substantially pure cis-unsaturated form meaning that the reagent contains at least about 80% of the cis-form. For example, the commercial oleyl alcohol is about 85% pure and most of the impurity consists of the trans analog (elaidyl alcohol).

The immune system, in both its innate and adaptive arms, is involved in regulating inflammation of every type, and inflammation is a key factor in processes such as wound healing, connective tissue re-modeling, angiogenesis, organ regeneration, neuroprotection, as well as in the adaptive immune responses seen in autoimmunity, allergies, graft rejection, and infection. Therefore, anti-inflammatory agents that modulate the inflammatory response such as those described here will be useful in a variety of conditions.

Inflammatory diseases, disorders or conditions that can be treated with the immunomodulators of the present invention include, but are not limited to, immunologically-mediated chronic or acute inflammatory diseases, disorders or conditions selected from an autoimmune disease, a severe allergy, asthma, or an inflammation associated with a disease, disorder or condition selected from graft rejection, a chronic degenerative disease such as Alzheimer's disease, neuroprotection, organ regeneration, chronic ulcers of the skin, or schizophrenia.

Examples of autoimmune diseases that can be treated according to the invention are multiple sclerosis or a human arthritic condition, e.g. rheumatoid arthritis, reactive arthritis with Reiter's syndrome, ankylosing spondylitis and other inflammations of the joints mediated by the immune system. Other autoimmune diseases are contemplated and are presented in the following list in the context of the organ or tissue involved.

Thus, the present invention relates to the treatment of an immunologically-mediated inflammatory disease, disorder or condition selected from myasthenia gravis, Guillain-Barré syndrome, or other inflammatory disease of the nervous system; psoriasis, pemphigus vulgaris or other diseases of the skin; systemic lupus erythematosus, glomerulonephritis or other disease affecting the kidneys; atherosclerosis or other inflammation of the blood vessels; autoimmune hepatitis, inflammatory bowel diseases e.g. Crohn's disease, pancreatitis, or other disorder of the gastrointestinal system; type 1 diabetes mellitus (insulin-dependent diabetes mellitus or IDDM), autoimmune thyroiditis (hashimoto's thyroiditis), or other disease of the endocrine system. In one preferred embodiment, the immunologically-mediated inflammatory disease, disorder or condition is psoriasis.

One of the models used to test the anti-inflammatory activity of the agents according to the invention is adjuvant arthritis (AA), an experimental disease of the joints inducible in some strains of rats by immunizing with *Mycobacterium tuberculosis* in complete Freund's adjuvant (CFA). These animals develop an arthritis whose features are similar to those of rheumatoid arthritis in humans and thus serve as animal models of human arthritic conditions such as rheumatoid arthritis, reactive arthritis in Reiter's syndrome, ankylosing spondylitis and other inflammations of the joints which appear to be mediated by the immune system. Adjuvant arthritis also serves as a model of immune-mediated inflammation in general including cell-mediated autoimmune reactions, graft rejection and allergic reaction. For example, treatments which can suppress rheumatoid arthritis include immunosuppressive agents such as corticosteroids, cyclosporin A, azathioprine, and other immunosuppressive agents which are broadly used in the treatment of autoimmune diseases. Therefore, suppression of adjuvant arthritis by a therapeutic agent indicates that the agent is potentially useful as a broad anti-inflammatory agent.

The present invention further relates to a pharmaceutical composition for the treatment of inflammation comprising a pharmaceutically acceptable carrier and a compound of the general formula I described hereinabove.

The pharmaceutical composition provided by the present invention may be in solid, semisolid or liquid form and may further include pharmaceutically acceptable fillers, carriers or diluents, and other inert ingredients and excipients. The composition can be administered by any suitable route such as, but not limited to, oral, topical, or parenteral e.g. by injection through subcutaneous, intravenous, intramuscular, or any other suitable route. Since many of the compounds are oily, they are preferably administered parenterally, more preferably subcutaneously. If given continuously, the compounds of the present invention are each typically administered by 1-4 injections per day or by continuous subcutaneous infusions, for example, using a mini-pump. The dosage will depend on the state of the patient and severity of the disease and will be determined as deemed appropriate by the practitioner.

For parenteral administration, the compounds may be formulated by mixing the compound at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Generally, the formulations are prepared by contacting the compound uniformly and intimately with liquid carriers or finely divided solid carriers or both. Then, if necessary, the product is shaped into the desired formulation. Preferably, the carrier is a parenteral carrier, more preferably a solution that is isotonic with the blood of the recipient. Examples of such carrier vehicles include water, saline, Ringer's solution, and dextrose solution. Non-aqueous vehicles such as fixed oils can be also useful, as well as liposomes. These preparations can be made by conventional methods known to those skilled in the art, for example as described in "Remington's Pharmaceutical Science", A. R. Gennaro, ed., 17th edition, 1985, Mack Publishing Company, Easton, Pa., USA.

In another aspect, the present invention relates to a method for the treatment of inflammation, particularly immunologically-mediated inflammation, which comprises administering to a patient in need an effective amount of a compound of formula I as defined hereinbefore.

In a further aspect, the invention relates to therapeutic compositions comprising an adjuvant of the formula Ia hereinbefore and an antigen. The antigen may be one that raises a humoral response such as a toxin, a bacterial or a viral antigen, or is preferably an antigen that raises a cellular response such as a peptide.

The therapeutic preparation may comprise an antigen useful for treatment of an autoimmune disease, a neurodegenerative disease such as Alzheimer's disease or Parkinson disease, a cancer such as melanoma, or an infectious disease including both bacterial and viral infections.

In a preferred embodiment, the therapeutic composition is for treatment of a T-cell mediated disease, disorder or condition and comprises an antigen that is recognized by inflammatory T cells associated with the pathogenesis of said T-cell mediated disease, disorder or condition.

In one more preferred embodiment, the therapeutic preparation comprises an antigen which is recognized by inflammatory T cells associated with the pathogenesis of a T-cell mediated disease, disorder or condition and said preparation causes shifting of an individual's T-cell cytokine response from $T_H1$ to $T_H2$.

The anti-inflammatory immunomodulators of the present invention form lipid emulsions that, when used as a vaccine adjuvant with the antigenic substance to which the T cells involved in the disease, disorder or condition being treated are active, serve to mediate a shift from a $T_H1$ T-cell response prior to treatment to a $T_H2$ T-cell response after treatment. This finding establishes that such lipid emulsions are tolerogenic biologically active carriers which can be used in vaccines for the treatment of any $T_H1$-mediated disease or condition. In such vaccines, the antigen provides the immunological specificity for a therapeutic effect while the biologically active carrier of the present invention provides the biological outcome, i.e. the $T_H1 \rightarrow T_H2$ shift. Because of the shift mediated by said biologically active carrier of the present invention, diseases, disorders and conditions with a spectrum of autoreactivities can be turned off with a single antigen/carrier combination capable of inducing the desired T-cell cytokine shift.

In a preferred embodiment in accordance with the present invention, the therapeutic preparation comprises an antigen and the anti-inflammatory immunomodulator adjuvant of formula Ia for the treatment of organ-specific autoimmune diseases which are mediated by $T_H1$ cells. Examples of such diseases include, but are not limited to, autoimmune diseases such as multiple sclerosis, type I diabetes mellitus, rheumatoid arthritis, and autoimmune thyroiditis.

The antigen used in the preparation is an antigen recognized by inflammatory T cells associated with the pathogenesis of said autoimmune disease and may be the whole protein involved in the disease process, a peptide derived from the sequence of such a protein, an altered peptide which has a single amino acid substitution in the epitope of the pathogenic autoantigen peptide, or any other peptide recognized by the inflammatory T cells associated with the disease.

Thus, for the treatment of multiple sclerosis (MS), the antigen could be MBP, MOG or PLP, or a peptide derived from the human MBP sequence such as the peptides MBP (75-95), MBP(86-95), and MBP(82-98) described in U.S. Pat. No. 5,817,629, or analogues thereof described in U.S. Pat. Nos. 5,948,764 and 6,239,499, or MOG peptides or PLP peptides and analogues, thereof, all these patents being hereby incorporated by reference as if fully disclosed herein. The antigen can also be glatiramer acetate, the generic name for the acetate salt of Copolymer 1 or Cop 1, a random copolymer composed of the four amino acids: tyrosine-glutamate-alanine-lysine, that cross-reacts functionally with MBP and is able to compete with MBP on the MHC class II in the antigen presentation. Glatiramer acetate has been approved in several countries for the treatment of MS under the trade name, COPAXONE® (a trademark of Teva Pharmaceuticals Ltd., Petah Tikva, Israel).

For the treatment of diabetes mellitus type I (IDDM), the peptide may be derived from glutamic acid decarboxylase (GAD), or GAD peptide analogues as described in U.S. Pat. No. 5,945,401, or insulin peptide analogues such as the peptides comprising residues 9 to 23 of the native insulin B chain sequence which are altered at position 12, 13, 15 and/or 16 and may be further altered as described in U.S. Pat. No. 6,197,926, all these patents being hereby incorporated by reference as if fully disclosed herein.

For the treatment of other autoimmune diseases the peptide will be derived from the sequence of an antigen associated with the disease or a peptide analogue thereof. Thus, for treatment of autoimmune thyroiditis, the peptide will be derived from the sequence of thyroglobulin; for rheumatoid arthritis the autoantigen can be derived from collagen II or from a Mycobacterium organism, e.g. *Mycobacterium tuberculosis*, e.g. the 60 kDa heat shock protein known as hsp60, which constitutes the mycobacterial epitope recognized by T lymphocytes in adjuvant arthritis, or the corresponding human HSP60 or a peptide thereof; for the treatment of myasthenia gravis, the peptide is derived from the sequence of the acetylcholine receptor or an analogue thereof as described in U.S. Pat. No. 6,066,621, hereby incorporated by reference as if fully disclosed herein; for the treatment of systemic lupus erythematosus the peptide may be derived from the sequence of the protein P53; and for the treatment of Guillain-Barré syndrome the peptide may be derived from the sequence of myelin antigen P2.

The antigen may be also a non-peptidic antigen. Examples of non-peptidic antigens that can be used according to the invention include, but are not limited to, phospholipids for the treatment of phospholipid syndrome, cholesterol for the treatment of atherosclerosis, and DNA molecules for the treatment of systemic lupus erythematosus.

It is not critical that the antigen be a peptide. Thus, for example, $T_H1$ mediated allergic responses which result in skin sensitivity and inflammation, such as contact dermatitis, can be treated by a vaccine containing the irritant antigen and a biologically active carrier/adjuvant in accordance with the present invention which will cause a shift in the cytokine response from a $T_H1$-type to a $T_H2$-type. Thus, while the patient will continue to have elevated antibody-levels against the antigen, the inflammatory T-cell response causing the skin irritation will be suppressed.

Accordingly, the tolerogenic biologically active carrier/adjuvant of the present invention may be used any time that it is desired to create tolerance for the antigen which the T cells are attacking, i.e., any time that a vaccine is being used to restrict a T-cell mediated condition, particularly a $T_H1$-cell mediated condition. If it can be determined which antigen is activating the response in graft rejection or in graft-versus-host disease, then the administration of such an antigen with a carrier in accordance with the present invention would be expected to facilitate the shift of the undesirable inflammatory $T_H1$ response to a more desirable $T_H2$ response, regardless of the overall complexity of the number of antigens to which T cells are active in such condition.

In one preferred embodiment of the present invention, the therapeutic preparation causes a, decrease in IL-2 or IFN-γ T-cell cytokine response and an increase in IL-4 or IL-10 T-cell cytokine response.

To determine the T-cell secretion of cytokines following activation with peptides, lymphocytes from the peripheral blood of patients are tested in an in vitro activation assay. Peripheral blood lymphocytes are isolated from whole heparinized blood by standard procedures and cultured with the test peptide(s) at concentration of 5-50 µg/ml. The supernatants from the cultured T-cells are collected at different time points and tested for activity of various cytokines, by ELISA or bioassay(s).

The finding according to the present invention that some esters of long-chain fatty alcohols with carboxylic acids containing a basic group may be used effectively as adjuvants for T-cell activation, is completely unexpected. Similarly, the discovery that these preparations are tolerogenic biologically active anti-inflammatory immunomodulators is also totally unexpected.

The advantage of the therapeutic preparation of the invention comprising an antigen and an immunomodulator of formula Ia as described herein as adjuvant resides in the fact that the treatment can be limited to the relatively short exposure required to induce a protective $T_H2$ immune response—the specific $T_H2$ immunity so induced will itself actively suppress the disease. Without the antigen, administration of the immunomodulator would have to be done chronically to continually suppress the inflammation, and the disease would be expected to reappear once treatment was stopped. In some diseases, the long-term effects of continued administration of an anti-inflammatory agent alone might be undesirable. Therefore, it is advantageous to induce active and specific regulation of the inflammatory process by combining an immunomodulator of the invention with a specific antigen.

The present invention further relates to a method of treating a T-cell mediated disease, disorder or condition, which comprises administering to an individual in need an effective amount of a therapeutic preparation comprising an antigen recognized by inflammatory T cells associated with the pathogenesis of said T-cell mediated disease, disorder or condition, and an adjuvant of the general formula Ia hereinabove.

The invention will now be illustrated by the following non-limitative Examples.

EXAMPLES

In the Examples herein, the following compounds will be identified by their numerals in bold as follows:

1. N,N-Dimethylamino-acetic acid octadec-(Z)-9-enyl ester;
2. Nicotinic acid octadec-(Z)-9-enyl ester;
3. (4-Methyl-piperazin-1-yl)-acetic acid octadec-(Z)-9-enyl ester tartrate;
4. (4-Methyl-piperazin-1-yl)-acetic acid octadecyl ester tartrate;
5. 4-dimethylaminomethyl-benzoic acid octadec-(Z)-9-enyl ester HCl
6a. 1-Methyl-3-octadec-(Z)-9-enyloxycarbonyl-pyridinium iodide;
6b. 1-Methyl-3-octadec-(Z)-9-enyloxycarbonyl-pyridinium chloride;
6c. 1-Methyl-3-octadec-(Z)-9-enyloxycarbonyl-pyridinium tosylate; and
7. 4-Methyl-4-octadec-(Z)-9-enyloxycarbonylmethyl-morpholin-4-ium chloride;
8. 1-[(2-(1H-indol-3-yl)-ethyl]-3-octadec-(Z)-9-enyloxycarbonyl-pyridinium bromide;
9. Piperazin-1-yl-acetic acid octadec-(Z)-9-enyl ester bitartrate;
10. 4-N,N-Dimethylaminomethyl-benzoic acid octadec-(E)-9-enyl ester HCl
11. α-Amino-α-phenyl-acetic acid octadec-(Z)-9-enyl ester HCl salt.

Example 1

Synthesis of N,N-dimethylamino-acetic acid octadec-(Z)-9-enyl ester (Compound 1)

N,N-Dimethylglycine (1.60 g, 15.4 mmol) was suspended in dry and alcohol-free chloroform (20 ml), and $PC_5$ (3.80 g, 17.3 mmol) was added. The yellow suspension was stirred at 55-60° C. for 1 h, cooled to 30° C., and oleyl alcohol (5.70 ml, 4.85 g, 18.0 mmol) was added. The yellow solution was heated to 63-65° C. and stirred at this temperature for 3-4 h. The solution was cooled to room temperature and a little amount of insoluble materials was filtered off. Water was added to the filtrate, and the pH of the mixture adjusted to 8. The organic phase was separated, washed with 5% $NaHCO_3$ and brine, dried and evaporated. The yellow oily residue (5.07 g) was triturated with ether and the resultant suspension was filtered. The filtrate was evaporated to dryness to give 3.18 g of a crude product, which was purified by column chromatography (n-hexane followed by ethyl acetate) to give the title compound, herein designated Compound 1, as a yellowish liquid (2.6 g, 7.36 mmol, 41%).

Calculated: C, 74.73; H, 12.26; N, 3.96. Found: C, 67.88; H, 11.69; N, 3.13.

$^1$H-NMR (200 MHz, $CDCl_3$) (ppm) δ: 0.88 (t, 3H, Me), 1.27-1.29 (m, 22H, 11$CH_2$), 1.57-1.67 (m, 2H, $CH_2$,), 2.00 (bd, 4H, 2$CH_2$), 2.37 (s, 6H, $NMe_2$), 3.18 (s, 2H, $CH_2$), 4.13 (t, 2H COO$\underline{CH_2}$), 5.31-5.39 (m, 2H, CH=CH).

IR: 1755 $cm^{-1}$ (CO).

Example 2

Synthesis of nicotinic acid octadec-(Z)-9-enyl ester (Compound 2)

Nicotinoyl chloride hydrochloride (17.8 g, 0.1 mol) and oleyl alcohol (26.85 g, 0.1 mol) were added into hexane (250 ml). Pyridine (15.8 g, 0.2 mol) was added to the stirred mixture over a period of 10 min, and the reaction mixture was stirred at room temperature for 24 h. Pyridine hydrochloride was removed by filtration and washed with hexane. The combined filtrate was extracted with water, dried over $MgSO_4$ and evaporated to dryness. The residue was digested twice with acetonitrile, and the sticky residue was dried to give a clear water-like liquid which turned soap-like upon cooling (21.1 g, 56.5 mmol, 56.5%).

$^1$H-NMR (200 MHz, CDCl$_3$) (ppm) δ: 0.90 (t, 3H, Me), 1.30-1.50 (m, 22H, 11CH$_2$), 1.75-1.85 (m, 2H, CH$_2$,), 2.00 (bd, 4H, 2CH$_2$), 4.35 (t, 2H, COOC$\underline{H}_2$), 5.31-5.39 (m, 2H, CH=CH), 7.41 (dd, 1H), 8.30 (dt, 1H), 8.77 (dd, 1H), 9.25 (d, 1H).

Example 3

Synthesis of (4-methyl-piperazin-1-yl)-acetic acid octadec-(Z)-9-enyl ester L-tartrate (Compound 3)

3a) Chloroacetic acid octadec-9-(Z)-enyl ester

Oleyl alcohol (147.9 g, 0.55 mol) was dissolved in n-hexane (300 ml), and chloroacetyl chloride (56.5 g, 0.50 mol) was added dropwise over 10 min. The clear reaction mixture was stirred for 24 h at room temperature. Traces of HCl gas were removed from the reaction mixture by bubbling nitrogen through it. This hexane solution of the crude title product was used in the next step without further purification.

3b) 4-Methyl-piperazin-1-yl-acetic acid octadec-9-(Z)-enyl ester (free base)

n-Hexane was added to the hexane solution obtained in Example 3a above (to a final volume of 500 ml), and 1-methyl-piperazine (103.6 g, 1.03 mol) was added. The reaction mixture was stirred for 36 h at room temperature. 1-Methylpiperazine HCl was removed by filtration and washed with n-hexane. The combined organic filtrates were extracted with water and brine, dried and evaporated under reduced pressure to give a pale yellow oil. The latter turned into a white solid when cooled to −20° C.

3c) 4-Methyl-piperazin-1-yl-acetic acid octadec-9-(Z)-enyl ester L-tartrate salt The free base of Example 3b above was dissolved in methanol (150 ml), and a solution of (L)-(+)-tartaric acid (75 g, 0.5 mol) in methanol (400 ml) was added. After stirring for 60 min at room temperature, the solution was filtered through a 20μ filter and evaporated to dryness. The sticky residue was first digested with acetonitrile, then treated with acetone for 24 h. The solvent was decanted off, and the solid was treated twice with acetone. The resultant suspension was dried under vacuum (filtration was avoided due to hygroscopicity of the wet tartrate salt). The dry product was homogenized and sieved (500μ) to give 197.3 g of the title Compound 3 as a yellowish powder (35 mmol, 64%), mp 69-72° C. Calculated: C, 62.34; H, 9.74; N, 5.01. Found: C, 60.33; H, 9.71; N, 4.91.

$^1$H-NMR (200 MHz, DMSO-d$_6$) ppm δ: 0.85 (t, 3H, Me), 1.18-1.24 (bs, 22H, 11CH$_2$), 1.54 (bs, 2H, CH$_2$), 1.96 (bs, 4H, 2CH$_2$), 2.56 (s, 3H, N-Me), 2.69 (s, 4H, 2CH$_2$), 2.90 (s, 4H, 2CH$_2$), 3.26 (s, 2H, N—CH$_2$COO), 4.0 (t, 2H, CH$_2$OCO), 4.18, (s, 1.5H, tartrate CH), 5.29 (t, 2H, CH=CH).

IR (cm$^{-1}$): 1616, 1739 (C=O).

Example 4

Synthesis of (4-Methyl-piperazin-1-yl)-acetic acid octadecyl ester L-tartrate (Compound 4)

Stearyl alcohol (27.2 g, 100 mmol) was dissolved in benzene (150 ml) and chloroacetyl chloride (8.0 ml, 100 mmol) was added dropwise over 10 min. The clear reaction mixture was stirred at room temperature for 48 h. Traces of HCl were removed by bubbling nitrogen gas. 1-Methyl-piperazine (28.0 ml, 250 mmol) was added, and the reaction mixture stirred at room temperature for 36 h. 1-Methylpiperazine HCl was removed by filtration and washed with n-hexane. The filtrate and washings were combined and extracted successively with water and brine, dried and evaporated to dryness, to give the free base (38.8 g). The latter was dissolved in ethanol and combined with a solution of (L)-(+)-tartaric acid (14.18 g) in ethanol (150 ml), stirred for 60 min and kept at room temperature for 3 days. The resultant solid was collected by filtration and dried to give 46.5 g (83 mmol, 83%) of the title Compound 4 as a white solid, mp: 88-9° C.

Calculated: C, 62.11; H, 10.07; N, 5.00. Found: C, 61.02; H, 10.39; N, 5.01.

$^1$H-NMR (200 MHz, DMSO-d$_6$) ppm δ: 0.85 (t, 3H, Me), 1.18-1.30 (bs, 30H, 15CH$_2$), 1.54 (m, 2H, CH$_2$), 1.96 (bs, 4H, 2CH$_2$), 2.56 (s, 3H, N-Me), 2.69 (s, 4H, 2CH$_2$), 2.90 (s, 4H, 2CH$_2$), 3.26 (s, 2H, N—CH$_2$COO), 4.02 (t, 2H, CH$_2$OCO), 4.18, (s, 1.5H, tartrate CH), IR: 1742 cm$^{-1}$ (C=O).

Example 5

Synthesis of 4-dimethylaminomethyl-benzoic acid octadec-(Z)-9-enyl ester HCl (Compound 5)

5a) 4-Dimethylaminomethyl-benzoic acid HCl

A suspension of 4-aminomethyl-benzoic acid (92.5 g, 0.61 mol) in 98% formic acid (127 ml, 3.36 mol) was heated under stirring to complete dissolution, and 37% formaldehyde (114 ml, 1.53 mol) was added. The solution was heated and kept at reflux temperature for 10 h. After cooling, 20% HCl (130 ml) was added, and the solution was evaporated to dryness. The white powder (131.5 g, 0.61 mol, ~100%) thus obtained was used in the next reaction without further purification.

5b) 4-Dimethylaminomethyl-benzoic acid octadec-(Z)-9-enyl ester HCl

Thionyl chloride (28.6 ml, 0.39 mol) was added to a stirred suspension of 4-dimethylaminomethyl-benzoic acid HCl (65.0 g, 0.3 mol) in acetonitrile (300 ml), refluxed for 1 h, and evaporated to dryness. The yellowish solid residue was suspended in acetonitrile (300 ml), oleyl alcohol (99.5 ml, 0.31 mol) was added, and the mixture was refluxed for 2 h. The mixture was allowed to cool, the crude salt was collected by filtration, washed with acetonitrile (500 ml), then acetone (300 ml), and dried to give 105 g (0.225 mol, 75%) of the title Compound 5 as a slightly yellowish solid, mp: 191-3° C.

Calculated: C, 72.15; H, 10.38; N, 3.00. Found: C, 71.32; H, 10.68; N, 3.15.

$^1$H-NMR (200 MHz, CDCl$_3$) ppm δ: 0.88 (t, 3H, Me), 1.25-1.33 (bs, 22H, 11CH$_2$), 1.75 (m, 2H, CH$_2$), 2.01 (m, 4H, 2CH$_2$), 2.83 (s, 6H, NMe$_2$), 4.30 (t, 2H, CH$_2$OCO), 4.39, (s, 2H, PhCH$_2$), 5.32-5.37 (t, 2H, CH=CH), 7.83 (d, 2H), 8.10 (d, 2H).

Example 6

Synthesis of Compounds 6a, 6b and 6c

6a) Synthesis of 1-methyl-3-octadec-(Z)-9-enyloxy-carbonyl-pyridinium iodide (Compound 6a)

Nicotinic acid octadec-(Z)-9-enyl ester, prepared by the procedure described in Example 2, (3.74 g, 10 mmol) and iodomethane (3.12 g; 22 mmol) were dissolved in a mixture of nitromethane (5 ml) and methanol (2.5 ml). The reaction mixture was kept at room temperature for 3 days and evaporated to dryness in vacuo. The residue was digested in hexane (20 ml), hexane was decanted off, and the residue dried to give the title compound as a yellow-orange sticky solid (4.95 g, 9.6 mmol, 96%).

$^1$H-NMR (200 MHz, DMSO-d$_6$) (ppm) δ: 0.85 (t, 3H, Me), 1.20-1.50 (m, 22H, 11CH$_2$), 1.70-1.80 (m, 2H, CH$_2$,), 1.96 (bd, 4H, 2CH$_2$), 4.36 (t, 2H, COOCH$_2$), 4.42 (s, 3H, N-Me), 5.27-5.39 (m, 2H, CH=CH), 8.25 (dd, 1H), 8.95 (dt, 1H), 9.20 (dd, 1H), 9.55 (d, 1H).

6b) Synthesis of 1-methyl-3-octadec-(Z)-9-enyloxy-carbonyl-pyridinium chloride (Compound 6b)

1-Methyl-pyridinium-3-carboxylate hydrochloride (1.74 g, 10 mmol) was added to thionyl chloride (7 ml). The reaction mixture was stirred at 68-70° C. for 1.5 h, then evaporated to dryness in vacuo. Hexane (25 ml) and oleyl alcohol (2.69 g, 10 mmol) were added to the residue, and the mixture was stirred at 43° C. for 3 days and evaporated to dryness under reduced pressure, to give 4.1 g (9.66 mmol, 96%) of a sticky solid.

$^1$H-NMR (200 MHz, DMSO-d$_6$) (ppm) δ: 0.85 (t, 3H, Me), 1.20-1.50 (m, 22H, 11CH$_2$), 1.70-1.80 (m, 2H, CH$_2$,), 1.95 (bd, 4H, 2CH$_2$), 4.38 (t, 2H, COOCH$_2$), 4.42 (s, 3H, N-Me), 5.27-5.40 (m, 2H, CH=CH), 8.25 (dd, 1H), 8.95 (dt, 1H), 9.20 (dd, 1H), 9.55 (d, 1H).

6c) Synthesis of 1-methyl-3-octadec-(Z)-9-enyloxy-carbonyl-pyridinium tosylate (Compound 6c)

Nicotinic acid octadec-(Z)-9-enyl ester, prepared by the procedure described in Example 2, (3.74 g, 10 mmol) was dissolved in a mixture of nitromethane (5 ml) and methanol (2.5 ml). A solution of methyl 4-methylbenzenesulfonate (1.86 g, 10 mmol) in a mixture of nitromethane (2 ml) and methanol (1 ml) was added, and the reaction mixture stirred at room temperature for 4 days. The clear solution was evaporated to dryness under reduced pressure to afford 5.2 g (9.3 mmol, 93%) of a clear sticky solid.

$^1$H-NMR (200 MHz, DMSO-d$_6$) (ppm) δ: 0.85 (t, 3H, Me), 1.20-1.50 (m, 22H, 11CH$_2$), 1.70-1.80 (m, 2H, CH$_2$,), 1.96 (bd, 4H, 2CH$_2$), 2.25 (s, 3H, tolyl Me), 4.36 (t, 2H, COOCH$_2$), 4.42 (s, 3H, N-Me), 5.27-5.39 (m, 2H, CH=CH), 7.10 (d, 2H, Ph), 7.45 (d, 2H, Ph), 8.25 (dd, 1H), 8.95 (dt, 1H), 9.20 (dd, 1H), 9.55 (d, 1H).

Example 7

Synthesis of 4-methyl-4-octadec-(Z)-9-enyloxycarbonylmethyl-morpholin-4-ium chloride (Compound 7)

Chloroacetic acid octadec-9-(Z)-enyl ester (17.2 g, 50 mmol) and N-methyl morpholine (6.6 ml, 60 mmol) were refluxed in acetonitrile (100 ml) for 18 h. The reaction mixture was cooled to room temperature and evaporated to dryness. Acetone was added, and the sticky residue which precipitated was collected by filtration, washed with acetone, and dried, to give the title Compound 7 as a slightly sticky and hygroscopic yellowish solid, mp 129-131° C. (4.11 g, 9.2 mmol, 18%).

Calculated: C, 67.31; H, 10.84; N, 3.14. Found: C, 65.58; H, 11.35; N, 3.48.

$^1$H-NMR (200 MHZ, CDCl$_3$) (ppm) δ: 0.88 (t, 3H, Me), 1.15-1.50 (m, 22H, 11CH$_2$), 1.65-1.80 (m, 2H, CH$_2$), 2.0 (bd, 4H, 2CH$_2$), 3.78 (s, 3H, N-Me), 4.08-4.36 (m, 10H, COO CH$_2$, 4CH$_2$ morpholine), 5.28 (s, 2H, COCH$_2$N), 5.27-5.39 (m, 2H, CH=CH).

Example 8

Synthesis of 1-[(2-(1H-indol-3-yl)-ethyl]-3-octadec-(Z)-9-enyloxy-carbonyl-pyridinium bromide (Compound 8)

A solution of 3-(2-bromoethyl)indole (1.12 g, 5 mmol) in methanol (10 ml) was added to a solution of nicotinic acid octadec-(Z)-9-enyl ester (1.87 g, 5 mmol) in methanol (5 ml). The reaction mixture was stirred at room temperature for 24 h and evaporated to dryness under reduced pressure to afford the title Compound 8 as a sticky solid (2.7 g, 4.5 mmol, 90.3%).

$^1$H-NMR (200 MHz, DMSO-d$_6$) (ppm) δ: 0.85 (t, 3H, Me), 1.20-1.50 (m, 22H, 11CH$_2$), 1.70-1.80 (m, 2H, CH$_2$,), 1.90-2.05 (bd, 4H, 2CH$_2$), 3.4 (2H, CH$_2$), 4.31 (t, 2H, CH$_2$OCO), 4.95 (t, 2H, CH$_2$), 5.30-5.39 (m, 2H, CH=CH), 6.30-7.60 (m, 5H, indole aryl), 8.10-9.50 (4H, pyr), 11.0 (br s, 1H, NH).

Example 9

Synthesis of piperazin-1-yl-acetic acid octadec-(Z)-9-enyl ester bitartrate (Compound 9)

To a solution of piperazine (10.77 g, 125 mmol) in acetonitrile (200 ml) was added a solution of crude oleyl chloroacetate (prepared from 25 mmol chloroacetyl chloride) in acetonitrile. The mixture was refluxed for 1.5 h, cooled to room temperature and evaporated to dryness. Water and ethyl acetate were added to the residue, and the phases were separated. The organic phase was washed with an equal volume of water, dried on sodium sulfate, and evaporated to dryness. The oily residue was dissolved in a small volume of methanol, and L-tartaric acid (7.50 g, 2 eqs.) in MeOH was added. The solution of the crude salt was evaporated to dryness, and the solid residue treated with acetonitrile, filtered, washed with acetonitrile, and then with acetone. The solid was dissolved in MeOH (400 ml), filtered and evaporated to dryness. The residue was treated with EtOAc, filtered, washed with EtOAc, then with acetone and dried to give the title Compound 9 as a white, non-hygroscopic powder, mp 130-132° C. (10.45 g, 15 mmol, 60%).

Calculated: C, 55.32; H, 8.42; N, 4.03. Found: C, 53.67; H, 8.66; N, 4.14.

$^1$H-NMR (200 MHz, DMSO-d$_6$) ppm δ: 0.85 (t, 3H, Me), 1.18-1.34 (bs, 22H, 11CH$_2$), 1.54 (bs, 2H, CH$_2$), 1.97 (bs, 4H, 2CH$_2$), 2.73 (s, 4H, 2CH$_2$), 3.06 (s, 4H, 2CH$_2$), 3.30 (s, 2H, N—CH$_2$COO), 4.03 (t, 2H, CH$_2$OCO), 4.22, (s, 1.5H, tartrate CH), 5.33 (t, 2H, CH=CH).

Example 10

Synthesis of 4-dimethylaminomethyl-benzoic acid octadec-(E)-9-enyl ester HCl (Compound 10)

The title Compound 10 (1.0 g, 2.1 mmol, 46%), mp: 194-6° C., was prepared from 4-dimethylaminomethyl-benzoic acid HCl (1.0 g, 4.6 mmol) by the procedure described in Example 5b, except that elaidyl alcohol was used instead of oleyl alcohol.

Calculated: C, 72.14; H, 10.37; N, 3.00. Found: C, 71.36; H, 11.01; N, 3.19.

$^1$H-NMR (200 MHz, CDCl$_3$) ppm δ: 0.88 (t, 3H, Me), 1.25-1.33 (bs, 22H, 11CH$_2$), 1.75 (m, 2H, CH$_2$), 1.96 (m, 4H, 2CH$_2$), 2.83 (s, 6H, NMe$_2$), 4.30 (t, 2H, CH$_2$OCO), 4.39, (s, 2H, PhCH$_2$), 5.38 (t, 2H, CH=CH), 7.83 (d, 2H), 8.10 (d, 2).

Example 11

Synthesis of aminophenylacetic acid octadec-(Z)-9-enyl ester HCl (Compound 11)

To a solution of N-Boc phenylglycine (2.51 g, 10 mmol) in acetonitrile (50 ml), was added portionwise 1,1'-carbonyldiimidazole (3.24 g, 20 mmol). The solution was stirred at room temperature for 1 h, oleyl alcohol (3.15 ml, 2.68 g, 10 mmol) was added, and the reaction mixture further stirred for 2 h at room temperature. The solvent was evaporated, the residue was dissolved in ethyl acetate (150 ml), washed successively with 5% NaHCO$_3$, 5% citric acid and water, dried on MgSO$_4$ and evaporated to dryness. The residue was dissolved in 1% HCl in ethyl acetate (100 ml), and the solution set aside for 6 h at room temperature, and evaporated to dryness. The residue thus obtained was crystallized from ether/n-hexane to give 1.6 g 3.65 mmol, 36.5%) of an off-white solid, mp 101-103° C.

Calculated: C, 71.28; H, 10.12; N, 3.10. Found: C, 70.87; H, 10.33; N, 3.47.

$^1$H-NMR (200 MHz, DMSO-d$_6$) (ppm) δ: 0.85 (t, 3H, Me), 1.20-1.50 (m, 22H, 11CH$_2$), 1.70-1.80 (m, 2H, CH$_2$,), 1.96 (bd, 4H, 2CH$_2$), 4.15 (m, 2H, COOCH$_2$), 5.25 (s, 1H, Ph CHNH$_2$), 5.27-5.39 (m, 2H, CH=CH), 7.40-7.60 (m, 5H, Ph), 9.20 (br s, 3H, N$^+$H$_3$).

Example 12

Effect of dimethylamino-acetic acid octadec-(Z)-9-enyl ester (Compound 1) on adjuvant arthritis (AA)

AA was induced by immunizing inbred female Lewis strain rats (groups of 8 rats obtained from Harlan-Olac), 8-9 weeks old, at the base of the tail with 0.1 ml of incomplete Freund's adjuvant (IFA, mineral oil containing an emulsifier; Sigma) containing 1 mg killed *Mycobacterium tuberculosis* (Difco). Arthritis of the limbs was noted to develop 12-14 days later and was scored on a scale of 0-16 summing the severity of the inflammation of each of the 4 limbs on a scale of 0-4, as described (Holoshitz et al., 1983). The peak of the arthritis usually was observed around day 26 after immunization.

One group of rats was treated intravenously (IV) on the day of immunization with 40 mg of Compound 1 in 0.5 ml of saline (triangles); another group was treated IV with the same amount of Compound 1 on day 14 after the onset of AA (circles), and a third group was treated with saline (squares). AA was scored on a scale of 0-16 by the degree of redness and swelling of each limb, on a scale of 0-4. The results shown in FIG. 1 are the mean+SE. As shown in FIG. 1, Compound 1 could protect the rats against the inflammation caused by AA.

Example 13

Anti-Inflammatory Effect of Dimethylamino-acetic Acid Octadec-(Z)-9-enyl ester (Compound 1)—protection against EAE EAE is an experimental autoimmune disease inducible in some strains of rats by immunization with myelin basic protein (MBP) in complete Freund's adjuvant (CFA) (in Lewis rats) or with an emulsion of the rat's spinal cord in incomplete Freund's adjuvant (IFA) (in DA rats). The animal experimental disease serves as a model for the human autoimmune disease multiple sclerosis. The disease develops in the animal about 12 days after immunization and is characterized by paralysis of various degrees due to inflammation of the central nervous system. In some strains, like the Lewis rat, the paralysis can last up to 6-7 days and the rats usually recover unless they die during the peak of their acute paralysis. In other strains of rats like the DA rat, the paralysis can be chronic and remitting.

For the induction and clinical assessment of EAE, spinal cord obtained from DA rats was frozen, thawed and minced thoroughly with a spatula before immunization. Rats were immunized by one subcutaneous injection (just under the skin) into the dorsal base of the tail with 200 μl emulsion prepared from 1:1 IFA (Difco, Detroit, Mich., USA) and antigen (volume/weight, i.e. 100 μl IFA/100 mg of whole spinal cord). IFA was complemented with 20 mg/ml of *Mycobacterium tuberculosis* strain 37RA (Difco) (=complete Freund's adjuvant, CFA). The emulsion was prepared by trituration with a gas-tight glass syringe and a needle, 1.2 mm diameter. Rats were regularly weighed and examined for clinical signs of EAE. A four-graded scale was used to assess clinical severity: 0, no paralysis; 1, tail weakness (hanging); 2, hind limb paralysis; 3, hind and fore limb paralysis; 4, severe total paralysis (Lorentzen et al., 1995).

Figure 2:
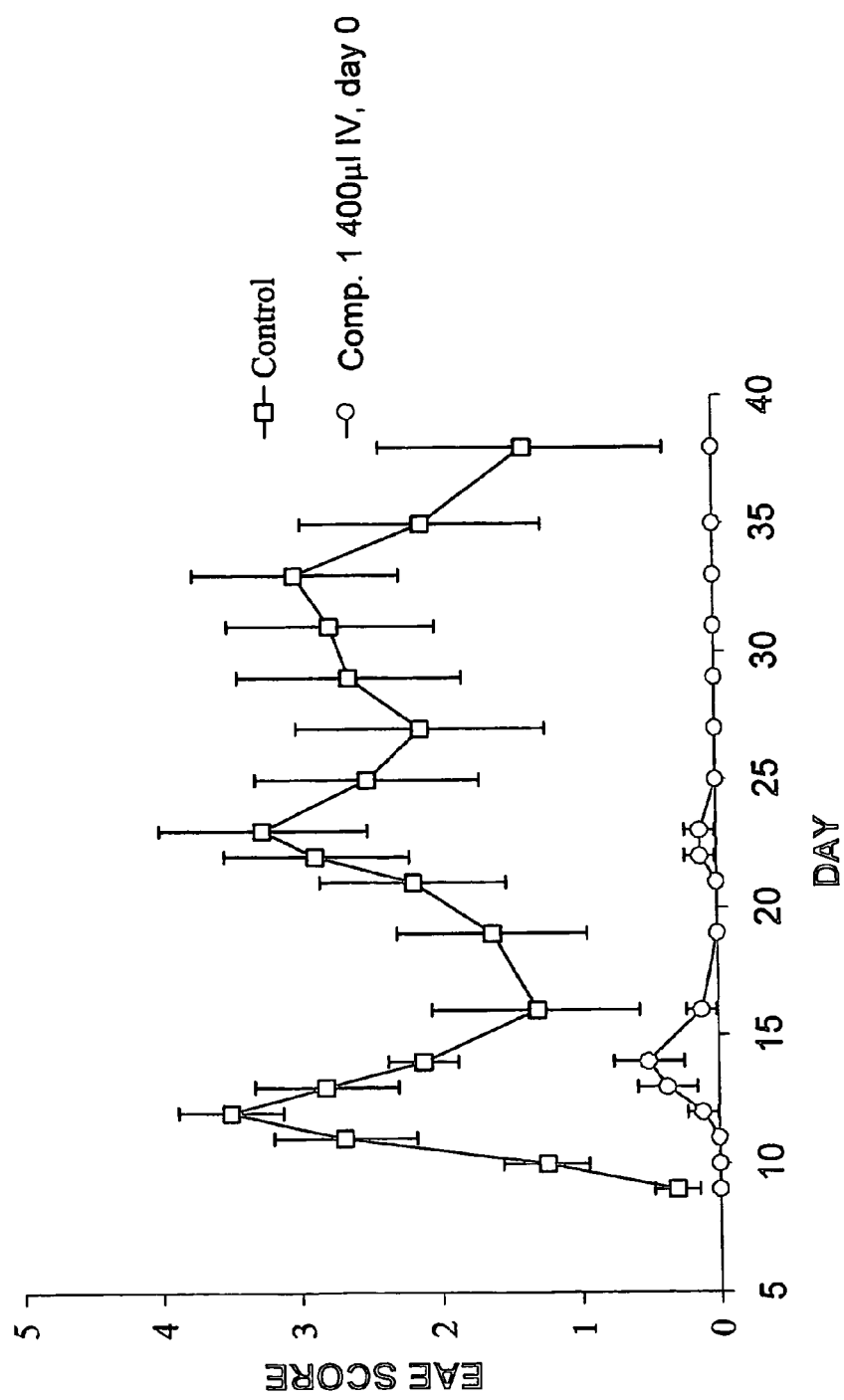
FIG. 2 shows the effect of Compound 1 on experimental autoimmune encephalomyelitis (EAE). Compound 1 was administered IV to DA rats on the day of immunization (day 0, circles).

Groups of 5 or 7 DA strain female rats, 8-9 weeks old, were immunized in the hind footpads with 0.1 ml per footpad of IFA containing 100 mg of whole, homogenized DA spinal cord, for a total of 200 mg per rat. On the day of immunization, the rats were treated by intravenous (IV) injection with 40 mg Compound 1 in 0.5 ml of saline or saline (control). The rats were scored for EAE on a severity scale of 0-4 as described above. The results are shown in FIG. 2 as the mean score+SE. The results in FIG. 2 show that Compound 1 (circles) could prevent the paralysis to a significant degree in comparison with the untreated control (squares) rats.

Example 14

Effect of dimethylamino-acetic acid octadec-(Z)-9-enyl ester (Compound 1) on skin allograft survival Skin graft transplantation was carried out essentially as described (Birk et al., 1999). Thus, mice were shaved and 1 cm$^2$ sections of skin were cut from the dorsal side of sacrificed donors and cleaned in phosphate-buffered saline (PBS). Two patches of dorsal skin, 1 cm$^2$ each, were cut from the anesthetized recipients (Nembutal 6 mg/ml, 0.25 ml/mouse) in preparation for the allograft. Two donor allografts per recipient were grafted onto the dorsal lesioned patches. Histoacryl (B. Braun Melsungen AG, Melsungen, Germany) was applied around the graft. Nobecutan (ASTR, Astra Tech, Glos G15, UK) was sprayed over the grafts.

Figure 3:
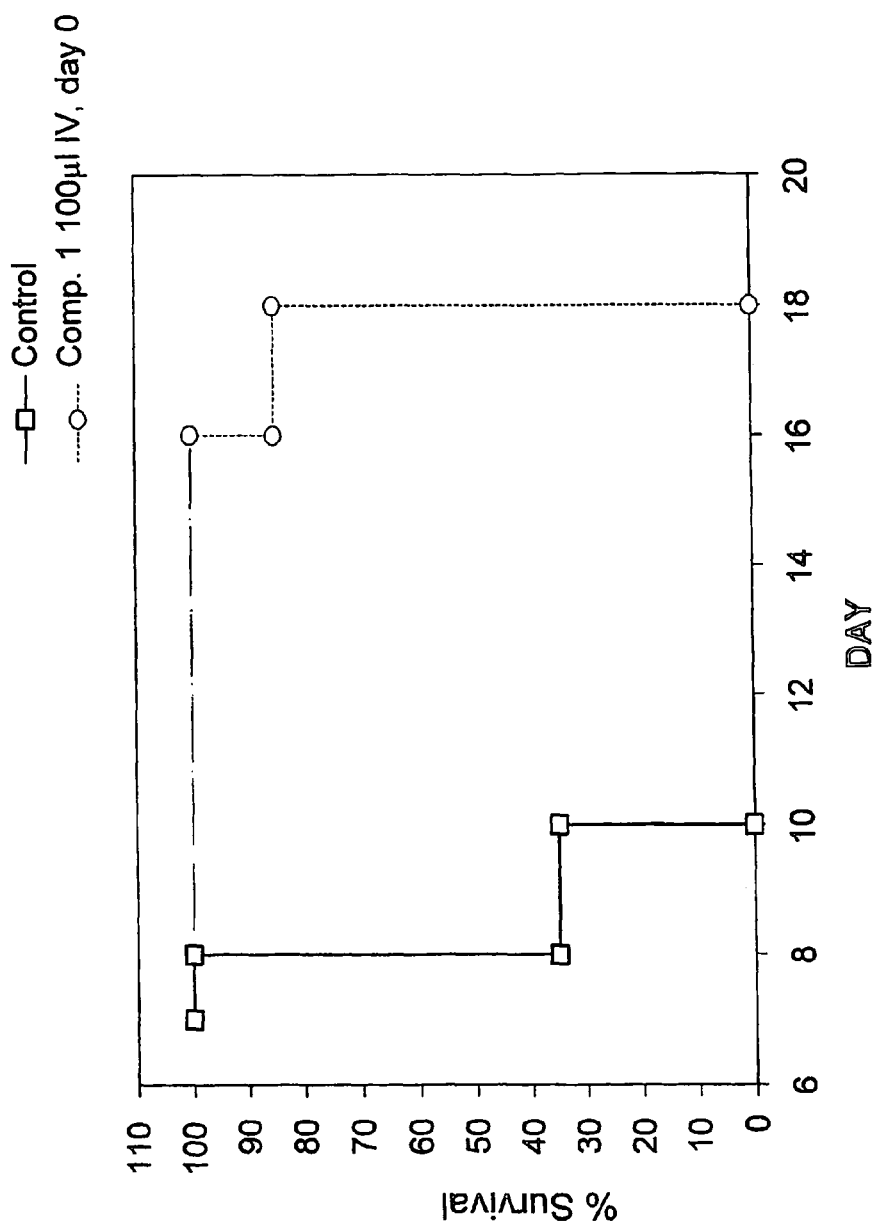
FIG. 3 shows the effect of Compound 1 on skin allograft survival. Compound 1 was administered IV to mice on the day of grafting (day 0, circles).

In the experiment, groups of 6 BALB/c female mice, 8 weeks old, were grafted with 1 cm$^2$, full thickness skin grafts from C57BL/6 female mice, 8 weeks old. On the day of grafting, a group of recipient mice was treated either with saline or IV with 100 μl saline containing 10 mg Compound 1. The day of rejection was scored. As shown in FIG. 3, the transplanted skin in the mice treated with Compound 1 (circles) survived longer in comparison with the untreated control (squares) mice.

Example 15

Use of dimethylamino-acetic acid octadec-(Z)-9-enyl ester (Compound 1) as an adjuvant for MBP peptide in the treatment of EAE Having shown that Compound 1 is a potent anti-inflammatory immunomodulator, it was of interest to test its effect as adjuvant together with an antigen recognized by inflammatory T cells associated with the pathogenesis of a T-cell mediated disease such as an autoimmune disease, for the treatment of said T-cell mediated disease. EAE was chosen as the model for MS and a MBP peptide was chosen as the antigen.

EAE is induced in 7-9 weeks old female Lewis rats by injecting each foot pad with 25 μg of guinea MBP (50 μg total) in CFA (Sigma). The disease develops about 12 days after immunization and is characterized by paralysis of various degrees due to inflammation of the central nervous system. The rats are scored for paralysis on a scale of 0-4, as described above in Example 13.

EAE is caused by T cells that recognize defined determinants of the MBP molecule. The major MBP determinant in the Lewis rat is composed of the peptide consisting of the sequence 71-90 of MBP (hereinafter p71-90 peptide).

In order to test whether administration of the encephalitogenic MBP p71-90 peptide with Compound 1 as adjuvant can also inhibit the development of EAE, Lewis rats, groups of 5-8, are treated with subcutaneous injections of the p71-90 peptide emulsified in 5 mg Compound 1 or in saline, or with Compound 1 in saline alone (without the peptide), on the day of MBP immunization (day 0) and five days later (day 5), or on day −14 and day −7 before immunization with MBP. The effect of the treatment with p71-90/Compound 1 on the EAE is assessed by measuring incidence and severity of the disease. A decrease in the maximal degree of paralysis compared to the control treatment with the p71-90 peptide in saline or with Compound 1 and saline without the peptide indicates that a relevant peptide such as p71-90 MBP peptide in an emulsion with Compound 1 is capable of modulating EAE in rats.

Example 16

Use of dimethylamino-acetic acid octadec-(Z)-9-enyl ester (Compound 1) as an adjuvant for recombinant hsp60 in the treatment of AA AA is induced in Lewis rats, 7-9 week old females, by immunization at the base of the tail with IFA containing 1 mg of killed *Mycobacteria tuberculosis* (Sigma; 0.1 ml of 10 mg/ml) as described in Example 12 above. The degree of joint inflammation is graded on a scale of 0-16.

For the treatment of AA, groups of 5-8 females Lewis rats aged 7-9 weeks, after induction of AA, are treated with 100 μg of recombinant hsp60, the mycobacterial epitope recognized by T lymphocytes in adjuvant arthritis in PBS or emulsified in Compound 1 (5 mg), or with Compound 1 in saline alone, by subcutaneous injection on the day of AA induction (day 0) and 7 days later (day+7), or on day −14 and −7. The effects of the treatment on joint inflammation are assayed as described in Example 12.

Example 17

(4-Methyl-piperazin-1-yl)-acetic acid octadec-(Z)-9-enyl ester tartrate (Compound 3) inhibits DTH skin reaction Delayed-type hypersensitivity (DTH), a localized inflammatory reaction induced by cytokines secreted by certain $T_H$ cells when they encounter certain types of antigens, is an established experimental model for skin inflammation.

Figure 4:
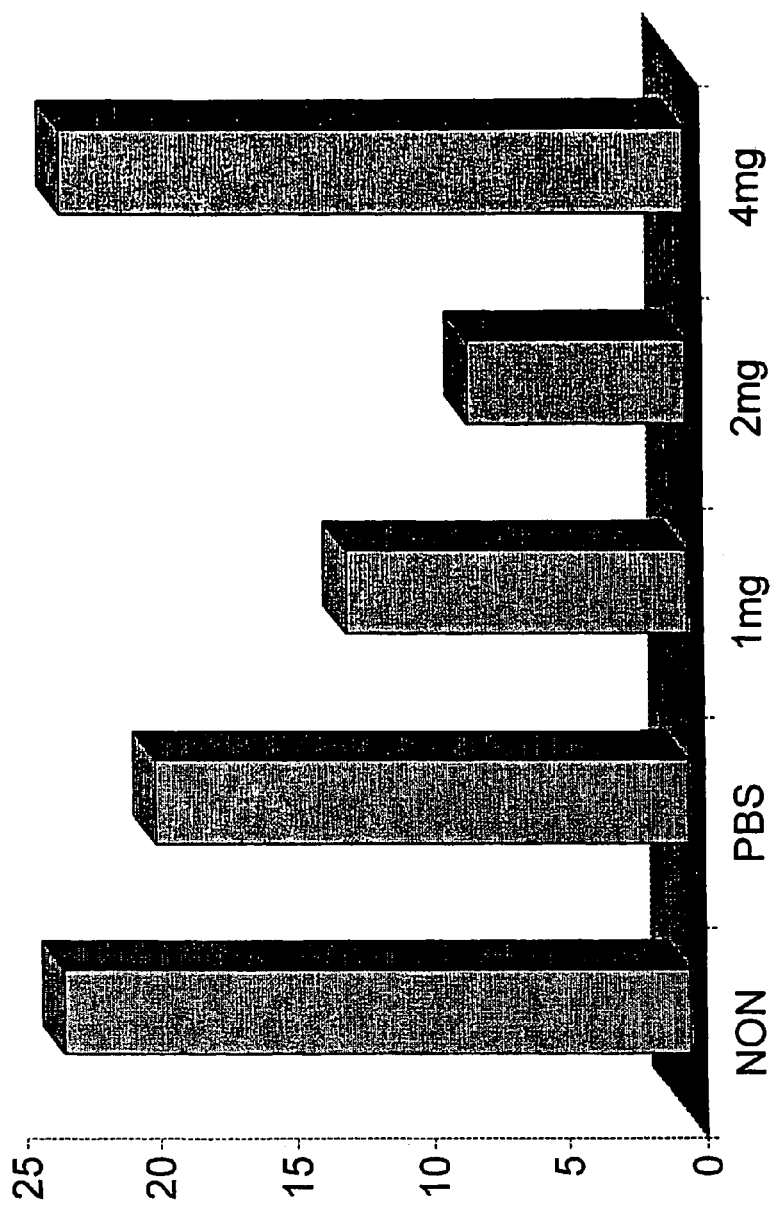
FIG. 4 shows inhibition of delayed-type hypersensitivity (DTH) reaction in BALB/c mice after treatment with different concentrations (1, 2 or 4 mg) of (4-methyl-piperazin-1-yl)-acetic acid octadec-(Z)-9-enyl ester tartrate (Compound 3).

As a first step, DTH reactions were induced in the skin of 8-week-old female BALB/c mice. The mice were sensitized by topical application of 200 μl of a 2% oxazolone (4-ethoxymethylene-2-phenyl-2-oxazolin-5-one; Sigma, St. Louis, Mo.) solution in acetone/olive oil (4:1, vol/vol) to the shaved abdomen of the mice. Six days after sensitization, one ear of each mouse was challenged by topical application of 20 μl of a 0.5% oxazolone solution. Treatment was given 30 min after the challenge by applying 20 μl of Compound 3 at various doses (1, 2 and 4 mg) on the challenged ear of each mouse (control: non-treated ear or treated with PBS). After 24 hours, the extent of inflammation was measured using the mouse ear-swelling test and the percent inhibition induced by the treatment with Compound 3 was quantitated. The results are shown in FIG. 4. Treatment with 1 mg and 2 mg Compound 3 inhibited the DTH reaction (12.5% and 8%, respectively).

Example 18

Compounds 5, 9, and 11 inhibit DTH Skin Reaction

Mice were induced with DTH as in Example 17. Treatment was given 30 min after the challenge by applying compounds 5, 9, and 11 in doses of 0.5, 1, 2, and 4 mg in 40 μl. In addition, a positive control of dexamethazone (2 mg/40 μl) was administered. A group of DTH induced mice was also treated with (4-Methyl-piperazin-1-yl)-acetic acid ethyl ester HCl (negative control.)

Figure 5:
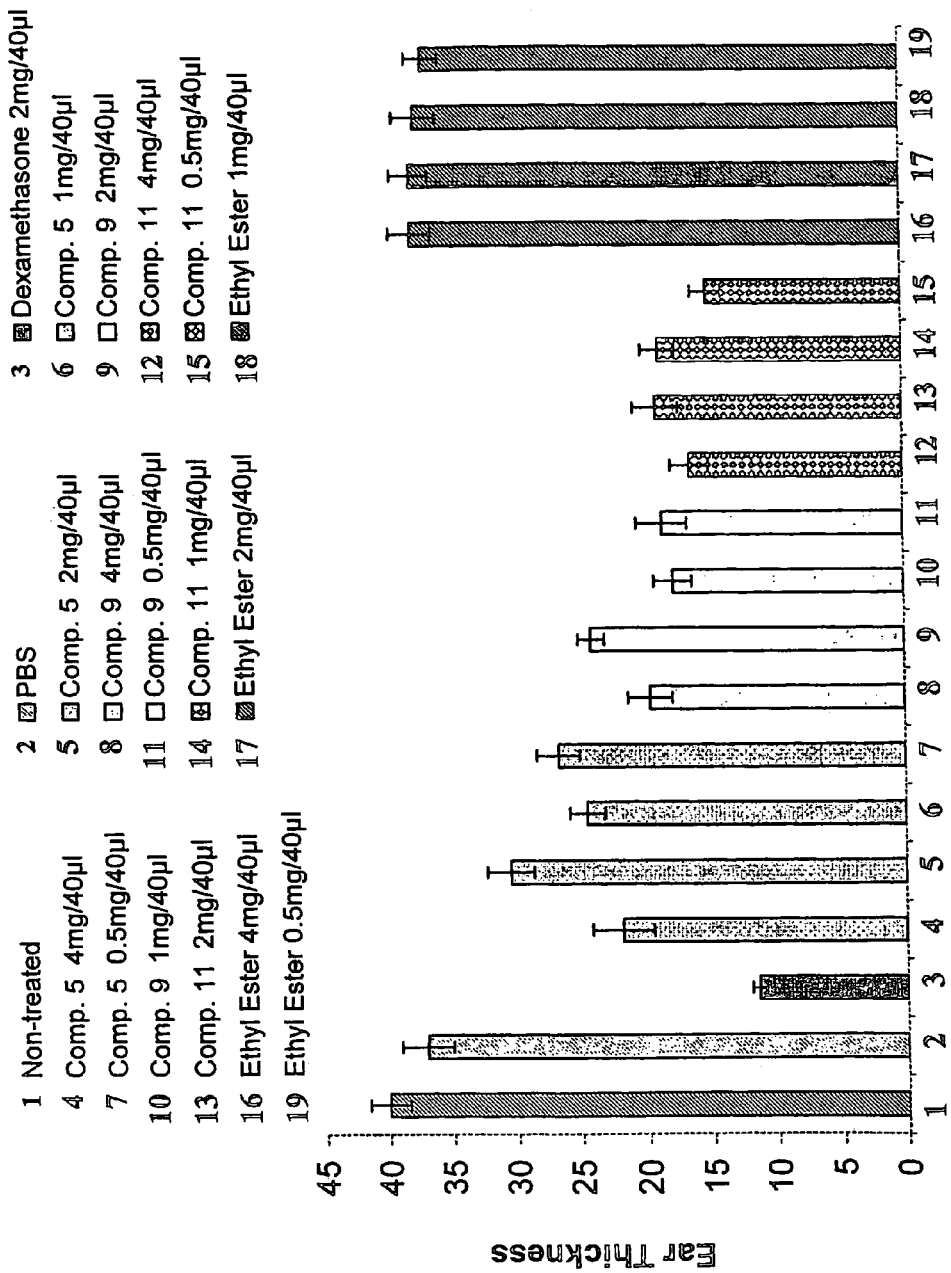
FIG. 5 shows the effect of different concentrations (0.5, 1, 2 or 4 mg) of Compounds 5, 9, and 11 on DTH in mice. Dexamethazone (2 mg) was used as positive control and (4-methyl-piperazin-1-yl)-acetic acid ethyl ester HCl (0.5, 1, 2 or 4 mg) as negative control.

The results of test compounds as well as dexamethazone showed positive results in reducing inflammation in the DTH model. The negative control, an ethyl ester, did not show any positive results. The results are shown in FIG. 5.

Example 19

Effect of Compound 3 on Adjuvant Arthritis (AA)

Figure 6:
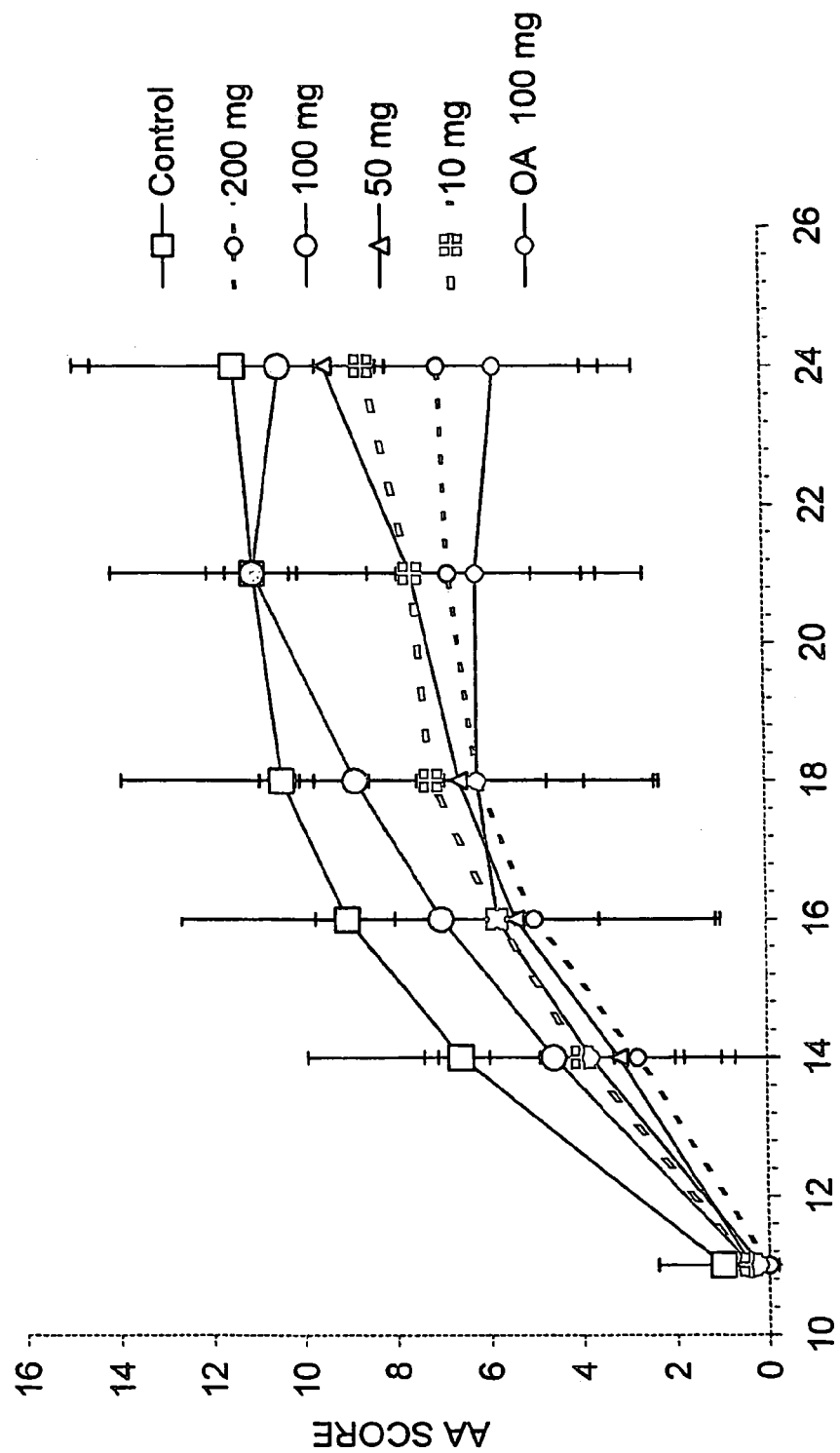
FIG. 6 shows the effect of subcutaneous (SC) administration of different concentrations (10, 50, 100, 200 mg) of Compound 3 on AA in rats. Oleyl alcohol (OA, 100 mg) was used for comparison.

AA was induced in 8-week-old female Lewis rats as described in Example 12 above. Groups of rats were treated with different amounts of Compound 3 (10, 50, 100 or 200 mg) SC at day −7 before induction of the disease. As shown in FIG. 6, Compound 3 could protect the rats against AA.

Example 20

Effect of Compound 3 SC and per os on EAE

EAE was induced in 8-week-old female Lewis rats as described in Example 15 above with guinea pig MBP in CFA.

Figure 7:
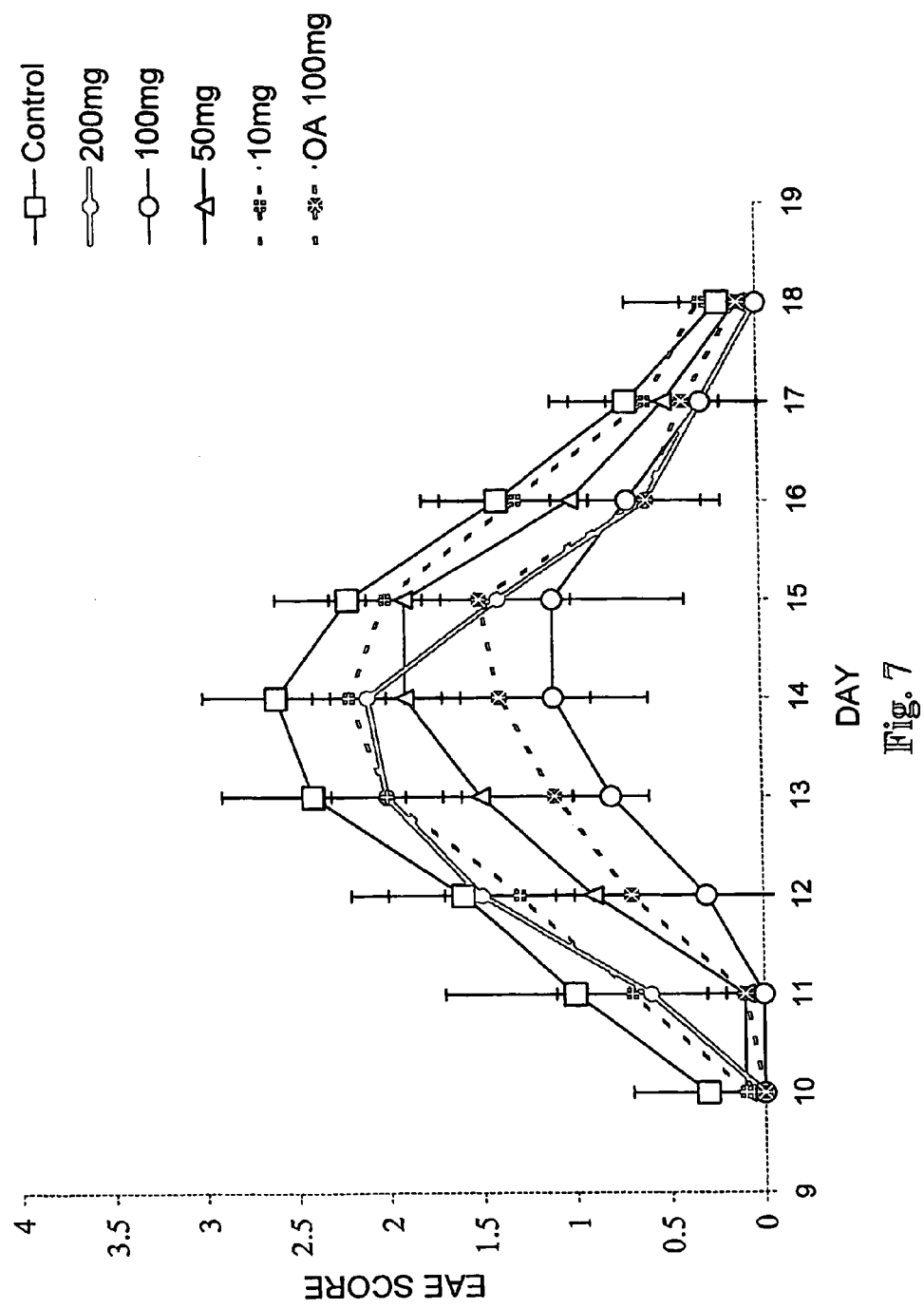
FIG. 7 shows the effect of SC administration of different concentrations (10, 50, 100, 200 mg) of Compound 3 on EAE in rats. Oleyl alcohol (OA, 100 mg) was used for comparison.

In one experiment, groups of rats (7 animals per group) were treated with different amounts of Compound 3 (10, 50, 100 or 200 mg) SC in the back on day 7 before induction of the disease. The rats were scored for EAE on a severity scale of 0-4 as described above. The results are shown in FIG. 7.

Figure 8:
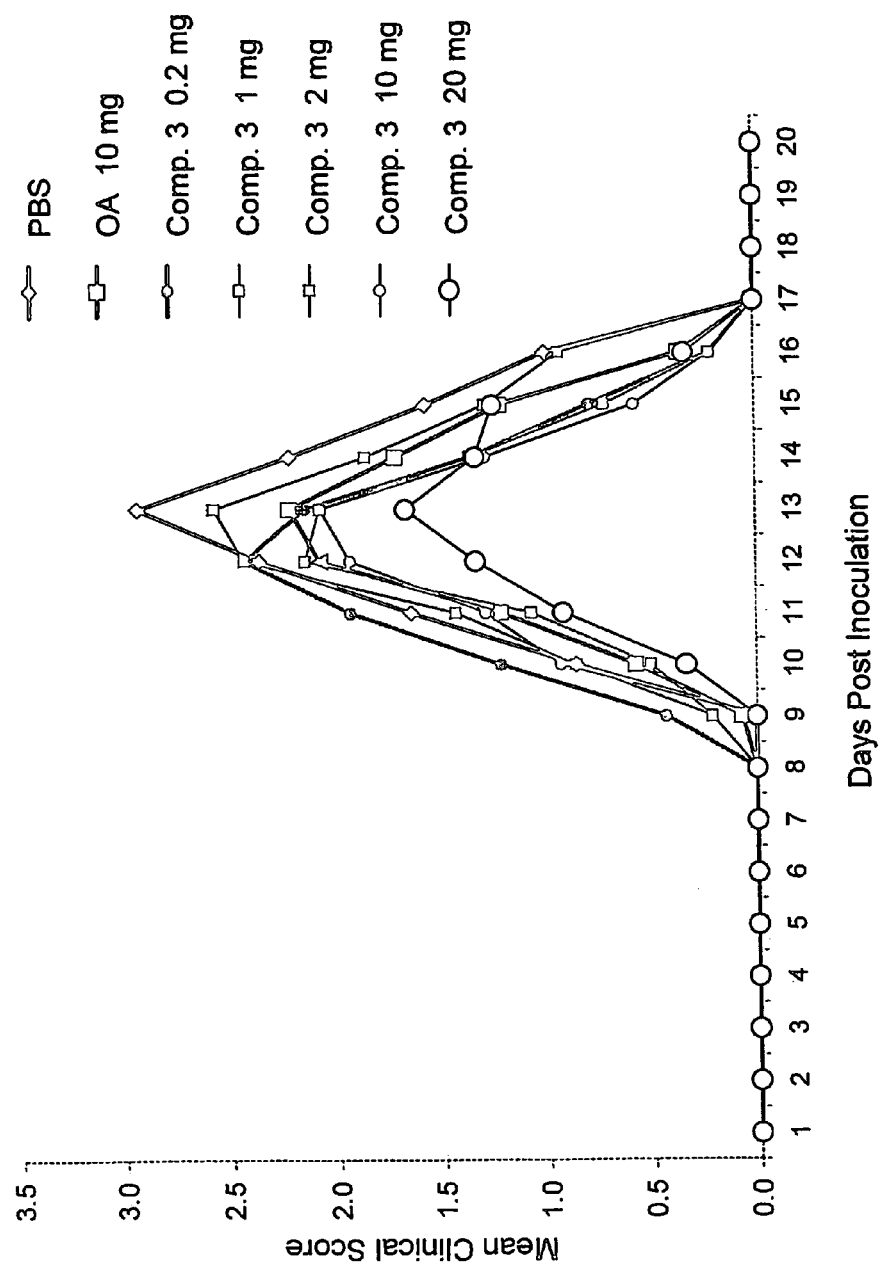
FIG. 8 shows the effect of per os administration of different concentrations (0.2, 1, 2, 10, 20 mg) of Compound 3 on EAE in rats. Oleyl alcohol (OA, 10 mg) was used for comparison.

In another experiment, groups of rats (7 animals per group) were treated with different amounts of Compound 3 (0.2, 1, 2, 10 or 20 mg) per os, every day, starting from the day of EAE induction. The rats were scored for EAE on a severity scale of 0-4 as described above. The results are shown in Table 1 and in FIG. 8.

In a further experiment, Compound 3 was administered per os every other day, starting from the day of EAE induction, and was found to be similarly effective (not shown).

The results of the experiments above show that Compound 3 could protect the rats against EAE when administered subcutaneously or orally.

TABLE 1

| Compound 3 Dose (mg) | Mean Clinic Score | % inhibition |
|---|---|---|
| 0 | 2.9 | 0 |
| 0.2 | 2.1 | 28 |
| 1 | 2.1 | 28 |
| 2 | 2.5 | 14 |
| 10 | 2.1 | 28 |
| 20 | 1.7 | 41 |

Example 21

Effect of Compound 9 per os on EAE

EAE was induced in 8-week-old female Lewis rats as described in Example 15 above with guinea pig MBP in CFA.

Figure 9:
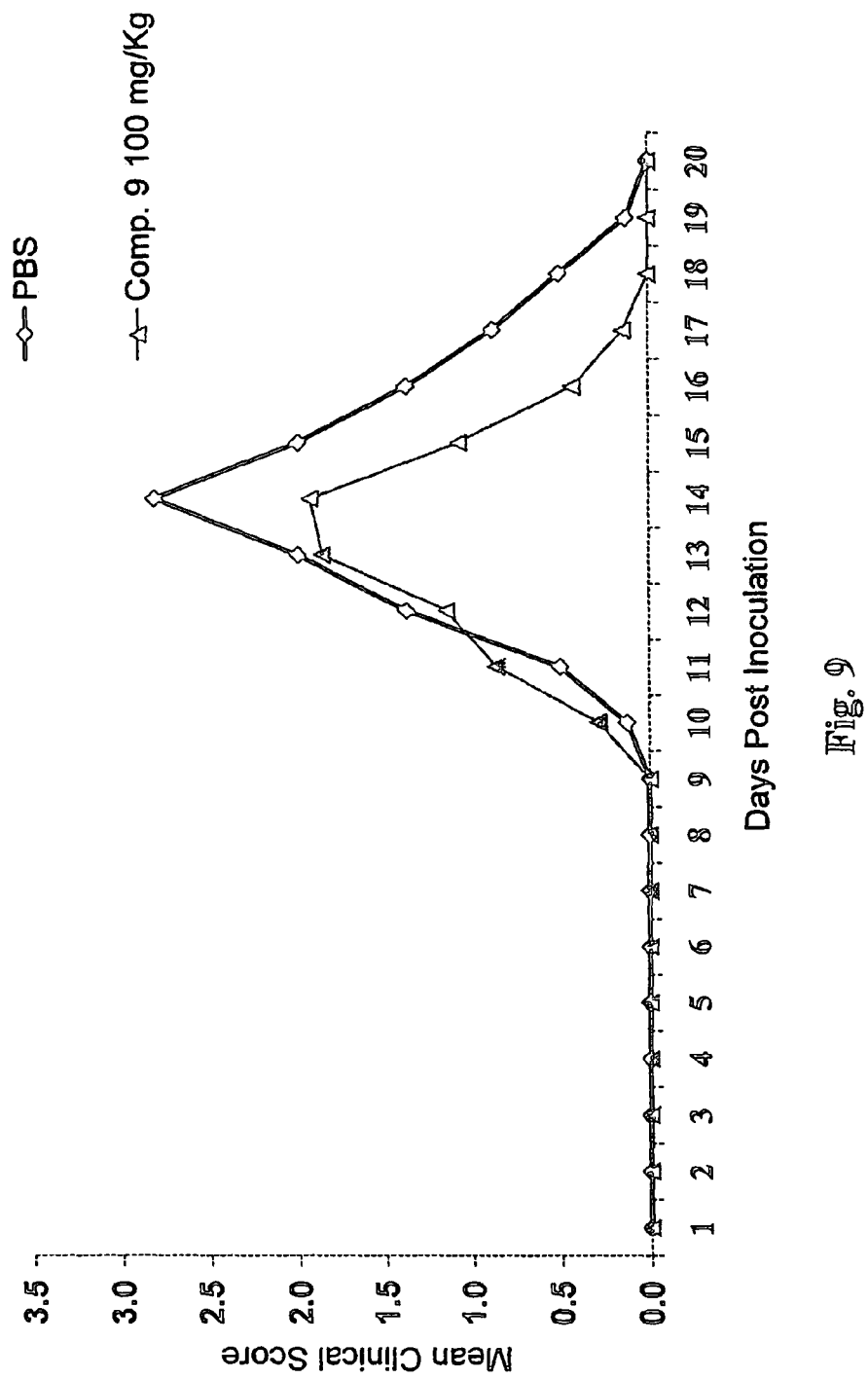
FIG. 9 shows the effect of per os administration of piperazin-1-yl-acetic acid octadec-(Z)-9-enyl ester bitartrate (Compound 9, 100 mg/kg) on EAE in rats.

Rats were treated with Compound 9 (100 mg/Kg) per os. The rats were scored for EAE on a severity scale of 0-4 as described above. The results in Table 2 and in FIG. 9 show that Compound 9 could protect the rats against EAE when administered orally.

TABLE 2

| DOSE | Mg/Kg | Mean Clinic Score | % Inhibition | % Sick rats | Mean onset |
|---|---|---|---|---|---|
| PBS | 0 | 2.81 ± 0.46 | 0 | 100 | 12.3 |
| Comp. 9 | 100 | 1.93 ± 0.45 | 31.4 | 100 | 11.5 |

Example 22

Compound 3 Promotes the Immunological Effects of Glatiramer Acetate (GA)

Glatiramer acetate (GA) is an immunomodulator used for the treatment of multiple sclerosis (COPAXONE®, a trademark of Teva Pharmaceuticals Ltd., Israel). GA has some well-defined immunological effects that can be demonstrated in vitro and in vivo: formation of GA specific T-cells and reduction in severity of clinical symptoms in EAE. Although these effects are seen with GA, its administration with certain additives may boost its effects. In the present example, the effect of immunization with GA and Compound 3 as an adjuvant was tested on EAE outcome and on the specific cellular immunological response.

Materials:

Glatiramer acetate (GA) was provided by Teva Pharmaceuticals Ltd., Israel; lyophilized mouse spinal cord homogenate (MSCH) from ICR mice was prepared by Biological Lab, Netanya, Israel; IFA, *M. tuberculosis* were purchased from Difco; CFA, pertussis toxin (PTX), PBS, 2-mercaptoethanol, concavalin A (Con A) were from Sigma; Trypan Blue from BDH; DCCM1 (Defined Cell Culture Media) and RPMI 1640 medium were from Beit-Haemek, Israel; L-glutamine 2 mM×100, MEM (Minimum Essential Media)—non-essential amino acids ×100, and sodium pyruvate 1 mM×100, all sterile, were from Bio-Lab, Israel.

Experimental Animals:

EAE was tested in CSJL/F1 mice, immunological response was tested in C57BL/J6 mice. Healthy, specific pathogen-free, female CSJLF/1 and male C57BL/J6 mice, were obtained from Harlan Animal Breeding Center, Jerusalem, Israel. The mice were 9-week old at the initiation of the study, weighing 20 g±15%.

A. Test Protocol for EAE (i) The mice were divided into 4 test groups as shown below:

| Group | Immunogen (mg/mouse) | Additive/Adjuvant | No. of mice |
|---|---|---|---|
| 1 | GA (5.0) | IFA | 10 |
| 2 | GA (5.0) | Compound 3 (0.5 mg/mouse) | 10 |
| 3 | — | Compound 3 (0.5 mg/mouse) + PBS (Vehicle - 0.1 mL/mouse) | 10 |
| 4 | — | PBS (Vehicle - 0.1 mL/mouse) | 10 |

(ii) Immunization:

Mice were immunized 11 days before EAE induction, with an emulsion of GA in IFA (group 1) or a solution of GA in Compound 3 (group 2), with Compound 3 in PBS (group 3) or with PBS alone (group 4), administered SC in the flanks, at a volume dose of 100 µL/mouse (at the right and left flanks, 50 µL/flank).

(iii) Preparation of GA Emulsion in IFA:

For immunization of group 1, a GA solution in PBS (100 mg/mL) was diluted 1:2 in IFA to yield a final concentration of 50 mg/mL for injection of 5.0 mg/mouse GA (0.1 ml). The GA+IFA mixtures were transferred into a syringe (2.5 mL) connected to a second syringe through a Luer lock bridge and mixed well by transferring the material from one syringe to another for about 10 minutes until the material was well emulsified.

(iv) Preparation of GA Solution with Compound 3:

For immunization of group 2, a solution of GA in PBS (100 mg/mL) was diluted in a solution of Compound 3 in PBS (10 mg/mL) to yield a final GA concentration of 50 mg/mL for dose of 5.0 mg/mouse GA. For immunization of control group 3, equal volumes of Compound 3 (10 mg/mL) and PBS (vehicle) were mixed. The final concentration of Compound 3 in the Compound 3+GA immunized group 2 and Compound 3 immunized control group 3 was 5 mg/mL (dose levels of 0.5 mg/mouse, equivalent to 25 mg/kg).

(v) EAE Induction:

EAE was induced by injecting the encephalitogenic agent consisting of MSCH and commercial CFA containing *Mycobacterium tuberculosis* H37Ra to the foot-pads of the animals and pertussis toxin IV.

(vi) Clinical Observation and Scoring:

The mice were observed for abnormal clinical signs and behavior, daily after immunization. They were weighed before immunization and once a week thereafter until the termination of the study. Ten days after induction of EAE, the mice were examined for EAE clinical signs and scored. The EAE clinical signs were observed and scored from the 9$^{th}$ day post-EAE induction until the termination of the experiment according to the following five-graded scale to assess clinical severity: 0, normal behavior; 1, weight loss; 2, tail weakness; 3, hind legs hypotonia and weakness; 4, hind legs paralysis; 4, severe total paralysis; 5, impaired respiration and/or convulsions and/or full paralysis or death. All rats having scores of 1 and above were considered sick.

(vii) Interpretation of Results:

Calculation of mortality: The number of sick and dead animals in each group was determined, and the incidence of disease and mortality rate was calculated as follows:

$$\text{Incidence of disease} = \frac{\text{No. of sick mice in group}}{\text{Total No. of mice in group}} \times 100$$

Calculation of percent activity: The percentage activity according to mortality was calculated as follows:

$$\% \text{ Inhibition} = \left(1 - \frac{\% \text{ of dead mice in treated group}}{\% \text{ of dead mice in control group}}\right) \times 100$$

Calculation of mean duration of disease and onset of disease: The mean duration of the disease and onset of disease expressed in days was calculated.

Calculation of the mean maximal score and percent inhibition: The maximal scores of each of the 10 mice in the test group were summed.

The mean maximal score (MMS) of the group was calculated as follows:

Σ maximal score of each mouse/number of mice in the group.

The percent inhibition was calculated as follows:

$$\text{Percent inhibition} = 1 - \left(\frac{MMS \text{ of treated group}}{MMS \text{ of control group}}\right) \times 100$$

Calculation of the mean group score and percent inhibition: The scores of each of the 10 mice in the test group was summed.

The mean group score (GMS) of the group was calculated as follows:

Σ scores of each mouse/number of mice in the group.
The percent inhibition was calculated as follows:

$$\text{Percent inhibition} = 1 - \left[\frac{GMS \text{ of treated group}}{GMS \text{ of control group}}\right] \times 100$$

B. Test Protocol for Immunological Follow Up (i) The mice were divided into 6 test groups as shown below:

| Group | Immunogen (μg/mouse) | Additive/Adjuvant | No. of mice |
|---|---|---|---|
| A | GA (75) | CFA + 5 mg/ml MT | 10 |
| B | GA (75) | — | 10 |
| C | — | Compound 3 (50 μg/mouse) | 10 |
| D | GA (75) | Compound 3 (50 μg/mouse) | 10 |
| E | — | Compound 3 (500 μg/mouse) | 10 |
| F | GA (75) | Compound 3 (500 μg/mouse) | 10 |

(ii) Immunization:

Mice were immunized 10 days prior to spleen collection. Emulsion of GA in CFA and solutions of PBS and GA with Compound 3 were administered SC in the flank, at a volume dose of 100 μL/mouse.

(iii) Preparation of GA Emulsion in CFA:

A solution of GA in PBS (final GA concentration of 1.5 mg/mL, for dose of 75 μg/mouse) was diluted in CFA to yield a final concentration of 0.75 mg/mL for dose of 75 μg/mouse GA. The mixtures (GA+CFA) were transferred into a syringe (2.5 mL) connected to a second syringe through a Luer lock bridge and mixed well by transferring the material from one syringe to another for about 10 minutes until the material is well emulsified.

(iv) Preparation of GA Solution with Compound 3:

Compound 3 was dissolved in PBS to yield 10 mg/ml for 500 μg/mouse, and diluted 1:10 to 1 mg/ml for 50 μg/mouse. GA (20 mg vial) was dissolved in PBS to yield 20 mg/mL solution, then further diluted in PBS to yield a final GA concentration of 1.5 mg/mL for dose of 75 μg/mouse. Equal volumes of Compound 3 and GA or PBS for control group were mixed.

(v) Safety Assessment:

To test new formulations for safety, a follow up was performed in which the mice were observed for abnormal clinical signs and behavior, daily after immunization. The mice were scored according to following chart: 0—normal behavior; 1—slight toxic signs (piloerection); 2—moderate toxic signs (partial eye lid closure, hunched posture, hypoactivity, apathy); 3—severe toxic signs (ataxia, convulsions, gasping respiration, paralysis, unconscious); 4—death. Mice were weighed before immunization and on the day of the termination of the study. On humane grounds, the study was terminated after 5 days of observation, due to 100% incidence of severe disease in all the groups. The spleens were weighed and spleen/body weight ratio was calculated.

(vi) Cell Culture:

Spleens were collected and pooled for each group in sterile RPMI medium. Cells were extracted resuspended in enriched DCCM1 medium and counted. Cells were then cultured with medium as baseline, two concentrations of GA as activator, 25 μg/ml and 5 μg/ml, and Con A as positive control, at 37° C., 5% $CO_2$. Supernatants were collected and tested for levels of cytokines secretion.

(vii) Detection of cytokine secretion in primary cultures from spleens was performed employing ELISA. Cells were activated in-vitro and IL-2 secretion levels were detected using commercial kits according to the provider's instructions.

C. Results (i) EAE Results

A summary of the mortality, mean maximal score, group mean score, mean onset and mean duration of disease is shown in Table 3. Suppression of EAE signs was noted in the group immunized with GA (5 mg/mouse)+. Compound 3. A 60% inhibition in mortality rate, a 16% decrease in MMS and a 23.7% reduction in GMS were found. This suppression of EAE signs in the group treated with GA+Compound. 3 was superior to the suppression seen in the groups treated with either Compound 3 without GA or with GA+IFA (another additive).

(ii) Immunological Follow Up Results

Figure 10:
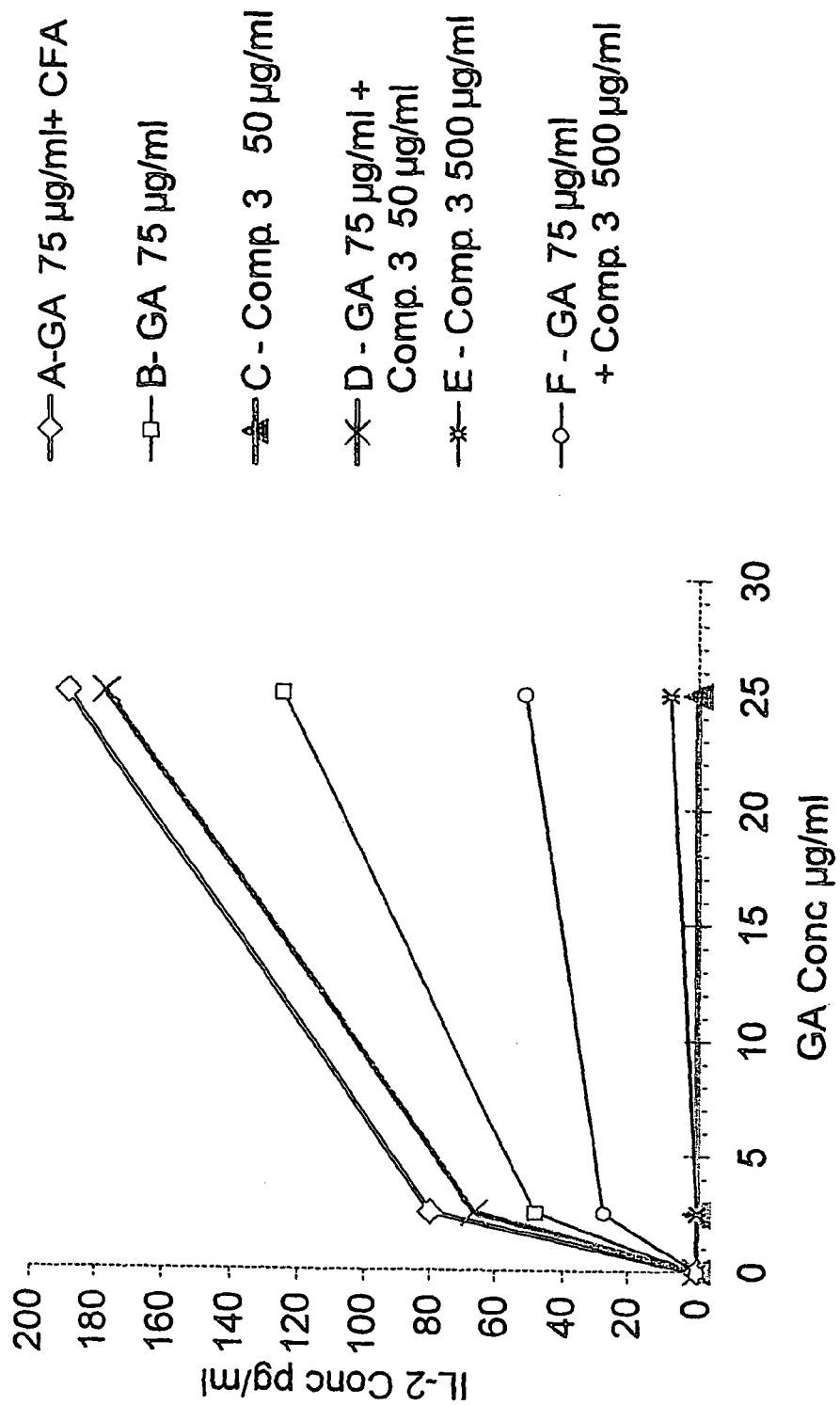
FIG. 10 shows that Compound 3 promotes the immunological effects of glatiramer acetate (GA) in EAE-induced mice.

IL-2 secretion from spleen cells of immunized mice is presented in Table 4 and in FIG. 10. In groups immunized with Compound 3 (without GA) in doses of 50 and 500 μg/mouse, IL-2 secretion from spleen cells was not elevated in response to GA. Con A (a non-specific activator) did increase IL-2 levels in all groups. There was no effect of Compound 3 on non-specific Con-A activation.

Immunization with GA 75 μg/mouse+Compound 3 in a dose of 50 μg/mouse caused IL-2 secretion from spleen cells in response to GA. IL-2 levels were higher than those found in spleen cells taken from mice immunized with GA alone.

Immunization with GA 75 μg/mouse+Compound 3 in a dose of 500 μg/mouse also caused IL-2 secretion from spleen cells in response to GA (although to a lesser extent than IL-2 levels found in spleen cells taken from mice immunized with GA alone).

Safety follow up showed no abnormal behavior or clinical signs. All scores were 0.

Compound 3 and GA 75 μg/mouse+Compound 3 in both doses had no adverse effect on mice weight. All mice showed similar, normal increase in weight of approximately 1.5 g/mouse in 10 days.

The ratio of spleen weight to total body weight of mice was similar in all groups.

D. Conclusions

The data presented here show that addition of Compound 3 to GA promotes its beneficial effects in the EAE model (particularly on survival) and promotes its immunological effects (cellular response of spleen cells to GA).

Treatment with Compound 3 with or without GA showed no signs of toxicological abnormalities. Therefore SC injection of Compound 3 has no detectable acute inflammatory or toxic effect. In addition, treatment with Compound 3 with or without GA showed no signs of immunosuppression.

Holoshitz, Y. et al., 1983. Lines of T lymphocytes mediate or vaccinate against autoimmune arthritis, *Science* 219: 56.

Kontogiorgis C. A., Hadjipavlou-Litinia D. J., and Schulz E., 2001, Antioxidant activity of DLω-phenyl-amino acid octyl esters with anti-inflammatory activity. *Arzneim-Forsch./Drug Res,.* 51 (I):485-488.

Lorentzen J. C. et al., 1995. Protracted, relapsing and demyelinating experimental autoimmune encephalomyelitis in DA rats immunized with syngeneic spinal cord and incomplete Freund's adjuvant, *J. Neuroimmunology.* 63: 193-205.

Markwardt F., Neuland P., and Klocking H.-P. 1966, Uber die antifibrinolytische Wirkung von Estern der 4-Aminomethylbenzoesaure (PAMBA) *Pharmazie* 21(6):345-348.

Metayer M M. M. et Jacob J., 1952, Preparation et propriétés pharmacodynamiques de quelques esters de la bétaine, *Ann. Pharm. Française,* 10:435-440.

Nixon-George A., Moran T., Dionne G., Penney C. L., et al. 1990, The adjuvant effect of stearyl tyrosine on a recombinant subunit hepatitis B surface antigen. *The Journal of Immunology,* 144(12): 4798-4802.

Penney C. L., Shah P., and Landi S., 1985, A simple method for the synthesis of long-chain alkyl esters of amino acids, *J. Org. Chem.* 50:1457-1459.

Penney C. L., Ethier D., Dionne G., Nixon-George A., Zaghouani H., et al., 993, Further studies on the adjuvanticity of stearyl tyrosine and ester analogues, *Vaccine* 11(11): 1129-1134.

TABLE 3

| Treatment group Dose (mg/mouse) | Mean Onset (days) | Mortality rate Dead total | inh.* 1 | MMS Value ± S.D. | inh.* 2 | GMS Value ± S.D. | inh.* 3 | Mean Duration (days) |
|---|---|---|---|---|---|---|---|---|
| IFA + GA 5.0 mg/mouse | 11.0 ± 1.1 | 8/10 | 0% | 4.8 ± 0.4 | .0% | 2.9 ± 1.0 | 3.7% | 4.0 ± 1.1 |
| Compound 3 + GA 5.0 mg/mouse | 10.6 ± 0.8 | 4/10 | 0% | 4.2 ± 0.8 | 6.0% | 2.9 ± 1.0 | 3.7% | 4.2 ± 0.8 |
| Compound 3 + PBS 0.1 mL/mouse | 10.3 ± 0.5 | 7/10 | 0% | 4.7 ± 0.5 | .0% | 3.3 ± 0.6 | 3.2% | 4.7 ± 0.5 |
| PBS (control) 0.1 mL/mouse | 10.1 ± 0.3 | 10/10 | | 5.0 ± 0.0 | | 3.8 ± 0.5 | | 4.9 ± 0.3 | inh.* = inhibition

TABLE 4

IL-2 Secretion from 5 × 10⁶ Spleen Cells of GA Immunized Mice

| Activator conc. (mg/mL) | A-GA 75 μg/m + CFA | B-GA 75 μg/m | C- Comp. 3 50 μg/m | D-GA 75 μg/m + Comp. 3 50 μg/m | E- Comp. 3 500 μg/m | F-GA 75 μg/m + Comp. 3 500 μg/m |
|---|---|---|---|---|---|---|
| 0 | UQL | UQL | UQL | UQL | UQL | UQL |
| 2.5 | 79.7 | 47.9 | UQL | 66.0 | UQL | 27.4 |
| 25.0 | 188.0 | 124.3 | UQL | 176.5 | 7.9 | 51.2 |
| Con A 2.5 | 426.8 | 419.6 | 426.8 | 425.1 | 426.8 | 387.7 |

REFERENCES

Beyer S. and Pilgrim H. 1991, Die Hemmung der Endothelzellproliferation durch Ester der 4-Aminomethylbenzoesaure (PAMBA), *Pharmazie* 46:597-599.

Birk et al., 1999. The 60 kDa heat shock protein modulates allograft rejection. *Proc. Nat. Acad. Science USA.* 96: 5159-63.

Rodriguez, M. D., Gomez, R., Sanchez, M and H. Garcia. 1998, *J. Appl. Toxicol.* 18: 313-6.

Rucka M., Oswiecimska M., Witek S. 1983, New biocides for cooling water treatment: Quaternary ammonium salts derivatives of glycine esters. *Environment Protection Engineering,* 9(3):25-31.

Schewe Ch., Schulz E., Vietinghoff G., Sprung W. D., Kobow M., Loose S., and Schewe T., 1991, On the mode of action of antiphlogistically active DL-ω-phenyl amino acid esters, *Biomed. Biochim. Acta,* 50(2):189-198.

Schulz E., Sprung W D, Kroning G. and Lauge, P. 1982, Pharmacological properties of D,L-2-phenylglycine alkyl esters with special consideration of their anti-inflammatory activity, *Agents Actions Suppl., AAS* 10:119-128.

Smith D. R., Maienthal M. and Eifert. R. L., 1951, Quaternary ammonium salts of heterocyclic bases, *JACS,* 73:2964-2965.

The Merck Index, 13th Edition, 2001, Merck & Co. Inc., Rahway, N.J., U.S.A.

Vetter W. and Meister W., 1981, Nicotinates as derivatives for the mass spectrometric investigation of long chain alcohols, *Organic Mass Spectrometry,* 16(3): 118-122.

Wong O., Huntington J., Nishihata T., and Rytting J. H., 1989, New alkyl N,N-dialkyl-substituted amino acetates as transdermal penetration enhancers, *Pharmaceutical Research,* 6(4):286-295.

The invention claimed is:

1. A compound of the general formula:

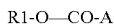

wherein
R1 is $C_{20}$-$C_{24}$ alkyl or $C_{16}$-$C_{18}$ alkenyl and A is a residue of the formula:

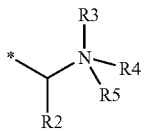

wherein R2 is H, $C_1$-$C_6$ alkyl, aryl, or aralkyl, wherein any aryl moiety may be unsubstituted or substituted by nitro, cyano, halo, hydroxy, NR6R7, or CR8R8NR6R7; R3 is H, a pair of electrons, or $C_1$-$C_6$ alkyl; R4 and R5 each is H or each is $C_1$-$C_6$ alkyl, or R4 and R5 together with the nitrogen atom to which they are attached form a 5-7 membered saturated ring optionally interrupted by an oxygen atom or by a nitrogen atom optionally substituted by $C_1$-$C_6$ alkyl; and R6, R7 and R8 each independently is H or $C_1$-$C_6$ alkyl, wherein: when R3 is a pair of electrons and R4 and R5 are each H, then R2 is $C_5$-$C_6$ alkyl, aryl, or aralkyl, wherein any aryl moiety may be unsubstituted or substituted by nitro, cyano, halo, NR6R7, or CR8R8NR6R7;

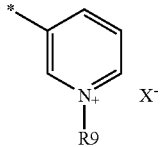

and pharmaceutically acceptable salts thereof.

2. The compound according to claim 1 wherein R1 is a $C_{16}$-$C_{18}$ alkenyl.

3. The compound according to claim 2, wherein R1 is cis-9-octadecenyl or trans-9-octadecenyl.

4. The compound according to claim 3 wherein R2 is H or phenyl, R3 is H or a pair of electrons, and R4 and R5 are methyl or together with the N atom to which they are attached form a morpholino or a piperazine ring optionally substituted at the nitrogen atom at position 4 by methyl.

5. The compound according to claim 4, which is selected from the group consisting of:
N,N-Dimethylamino-acetic acid octadec-(Z)-9-enyl ester;
(4-Methyl-piperazin-1-yl)-acetic acid octadec-(Z)-9-enyl ester tartrate;
4-Methyl-4-octadec-(Z)-9-enyloxycarbonylmethyl-morpholin-4-ium chloride; and
Piperazin-1-yl-acetic acid octadec-(Z)-9-enyl ester bitartrate.

6. The compound according to claim 1 wherein R1 is cis-9-octadecenyl, R2 is phenyl, R3 is a pair of electrons and R4 and R5 is each H.

7. The compound of claim 6 which is α-amino-α-phenyl-acetic acid octadec-(Z)-9-enyl ester HCl salt.

8. A pharmaceutical composition comprising a compound according to claim 1 or a pharmaceutically acceptable salt thereof, and a pharmaceutically acceptable carrier.

9. A pharmaceutical composition according to claim 8 for the treatment of multiple sclerosis, human arthritic condition, an inflammation associated with graft rejection or chronic ulcers of the skin.

10. A therapeutic composition comprising an antigen and as an adjuvant a compound of the formula R1-O—CO-A as defined in claim 1.

11. The pharmaceutical composition according to claim 9, for treatment of multiple sclerosis or a human arthritic condition.

12. The pharmaceutical composition according to claim 11, wherein said human arthritic condition is rheumatoid arthritis, reactive arthritis with Reiter's syndrome, ankylosing spondylitis or other inflammation of the joints mediated by the immune system.

13. A method for treating multiple sclerosis, a human arthritic condition, an inflammation associated with graft rejection or chronic ulcers of the skin in a patient comprising administering to the patient the pharmaceutical composition of claim 8.

14. The method of claim 13, wherein in compound in the pharmaceutical composition R1 is cis-9-octadecenyl, R2 is phenyl, R3 is a pair of electrons and R4 and R5 is each H.

15. The method of claim 14, wherein the compound in the pharmaceutical composition is α-amino-α-phenyl-acetic acid octadec-(Z)-9-enyl ester HCl salt.

16. The method of claim 14, for treating multiple sclerosis or a human arthritic condition.

17. The method of claim 16, wherein the human arthritic condition is rheumatoid arthritis, reactive arthritis with Reiter's syndrome, ankylosing spondylitis or other inflammation of the joints mediated by the immune system.

* * * * *